US009163228B2

(12) United States Patent
Fabis et al.

(10) Patent No.: US 9,163,228 B2
(45) Date of Patent: Oct. 20, 2015

(54) METHOD FOR ISOLATING AND PURIFYING NUCLEIC ACIDS

(75) Inventors: Roland Fabis, Hilden (DE); Markus Müller, Hilden (DE); Jörg Hucklenbroich, Hilden (DE); Mario Scherer, Hilden (DE)

(73) Assignee: QIAGEN GmbH, Hilden (DE)

( * ) Notice: Subject to any disclaimer, the term of this patent is extended or adjusted under 35 U.S.C. 154(b) by 197 days.

(21) Appl. No.: 13/639,808

(22) PCT Filed: Apr. 8, 2011

(86) PCT No.: PCT/EP2011/055552
§ 371 (c)(1),
(2), (4) Date: Oct. 5, 2012

(87) PCT Pub. No.: WO2011/124705
PCT Pub. Date: Oct. 13, 2011

(65) Prior Publication Data
US 2013/0030163 A1     Jan. 31, 2013

(30) Foreign Application Priority Data
Apr. 8, 2010 (EP) .................................... 10003759

(51) Int. Cl.
*C12N 15/10*     (2006.01)
(52) U.S. Cl.
CPC .......... *C12N 15/1003* (2013.01); *C12N 15/101* (2013.01)
(58) Field of Classification Search
CPC ......................... C12N 15/101; C12N 15/1003
See application file for complete search history.

(56) References Cited

U.S. PATENT DOCUMENTS

| | | | |
|---|---|---|---|
| 4,035,234 A | 7/1977 | Schutt | |
| 5,393,672 A | 2/1995 | Ness et al. | |
| 5,552,325 A | 9/1996 | Nochumson et al. | |
| 5,654,179 A | 8/1997 | Lin | |
| 5,817,765 A * | 10/1998 | Isaksson et al. | 530/364 |
| 5,877,141 A * | 3/1999 | Gabriel et al. | 510/392 |
| 2002/0040873 A1 | 4/2002 | Wahlberg et al. | |
| 2006/0084130 A1 | 4/2006 | Deslys et al. | |
| 2006/0188892 A1 | 8/2006 | Latham et al. | |
| 2008/0033160 A1 * | 2/2008 | Yang | 536/25.41 |
| 2009/0232808 A1 | 9/2009 | Priest et al. | |
| 2010/0331534 A1 * | 12/2010 | Khan et al. | 536/23.1 |
| 2013/0023655 A1 | 1/2013 | Fabis et al. | |
| 2013/0030165 A1 | 1/2013 | Fabis et al. | |
| 2013/0172539 A1 * | 7/2013 | Miyagi et al. | 530/412 |

FOREIGN PATENT DOCUMENTS

| | | | |
|---|---|---|---|
| EP | 0 261 956 A2 | 3/1988 | |
| EP | 1 245 674 A2 | 10/2002 | |
| EP | 1 743 939 A2 | 1/2007 | |
| EP | 2 270 151 A1 | 1/2011 | |
| WO | 95/24498 A1 | 9/1995 | |
| WO | 96/00228 A1 | 1/1996 | |
| WO | WO 9636706 A1 * | 11/1996 | ............. C12N 15/10 |
| WO | 99/16869 A1 | 4/1999 | |
| WO | 2006/130632 A2 | 12/2006 | |
| WO | 2007/050327 | 5/2007 | |
| WO | 2009/127350 A1 | 10/2009 | |
| WO | 01/94574 A2 | 12/2013 | |

OTHER PUBLICATIONS

BioGenex "Safety Data Sheet—EZ Dewax Solution, Ready to Use," XP-002602420, 90 pages (Oct. 30, 2003).
Buesa, R.J. et al., "Histology without xylene," *Annals of Diagnostic Pathology* 13:246-256 (2009).
Epicentre Biotechnologies—SoilMaster™ DNA Extraction Kit, Cat. Nos. SM02050, SM02005, SC04350, and SR04350, XP002604830, Retrieved from the Internet: URL:http://www.epibio.com/pdftechlit/178p10310, (Retrieved on Jun. 9, 2010) 4 pages (Mar. 29, 2010).
GE Healthcare, Data Sheet "Sephacryl High Resolution media HiPrep Sephacryl HR columns," Data File 18-1060-88 AD (2008).
Macherey-Nagel, Viral DNA/RNA Isolation, User Manual, NucleoSpin® 8 Virus, Nucleospin® 8 Virus Core Kit, 30 pages (Mar. 2010).
Okello et al., "Comparison of methods in the recovery of nucleic acids from archival formalin-fixed paraffin-embedded autopsy tissues," *Analytical Biochemistry* 400(1):110-117 (2010).
Qiagen, QIAamp® DNA Stool Mini Kit Handbook, XP002604829, 40 pages (Aug. 2001).
Qiagen, User-Developed Protocol: Purification of viral RNA and DNA from 1000 µl of plasma, serum, and cell-free body fluids using the QIAmp® MinElute® Virus Vacuum Kit, XP002587174, 6 pages (Jun. 2004).
USB Corp., PrepEase® Tissue & Cells DNA Spin Kit, Product Nos. 78860, 78861, 78862, Brief Protocol, XP002587173, 2 pages (2008).
Zhou et al., "DNA Recovery from Soils of Diverse Composition," *Applied and Environmental Microbiology* 62(2):316-322 (Feb. 1996).
Forcic et al., "Purification of genomic DNA by short monolithic columns," *Journal of Chromatography A* 1065:115-120, 2005.
Hanselle et al., "Isolation of genomic DNA from buccal swabs for forensic analysis, using fully automated silica-membrane purification technology," *Legal Medicine* 5:S145-S149, 2003.
Heilig et al., "Large-Scale Preparation of Plasmid DNA.," *Current Protocols in Molecular Biology*, Chapter 1, Units 1.7.1-1.7.16, 1998.

(Continued)

*Primary Examiner* — Jonathan S Lau
(74) *Attorney, Agent, or Firm* — Seed IP Law Group PLLC

(57) ABSTRACT

The present invention relates to a method for isolating and purifying nucleic acids, preferably comprising genomic DNA, from biological samples comprising the steps of lysing the sample using a lysis buffer comprising a source of anionic surfactant ions, optionally disintegrating the RNA present in the lysate, precipitating the surfactant ions from the lysate, and separating the nucleic acids from the precipitate and further contaminants by size-exclusion chromatography. The invention furthermore relates to a lysis buffer, a method of lysing cells and a kit for the isolation and purification of nucleic acids.

21 Claims, 10 Drawing Sheets

(56) References Cited

OTHER PUBLICATIONS

Prodělalová et al., "Isolation of genomic DNA using magnetic cobalt ferrite and silica particles," *Journal of Chromatography A 1056*:43-48, 2004.

"Fungus," Wikipedia.com (accessed Jun. 3, 2013) (28 pages).

"How Many Species of Bacteria Are There?" wisegeek.com (accessed Sep. 23, 2011) (2 pages).

"Mammal," Wikipedia.com (accessed Sep. 22, 2011) (17 pages).

"Murinae," Wikipedia.com (accessed Mar. 18, 2013) (21 pages).

"Plant," Wikipedia.com (accessed Mar. 8, 2013) (12 pages).

Sambrook, Joseph, et al. (eds.), Molecular Cloning: A Laboratory Manual: Third Edition—vol. 1, Cold Spring Harbor Laboratory Press, New York, "Protocol 8: Purification of Plasmid DNA by Precipitation with Polyethylene Glycol" (2001) (5 pages).

"Virus," Wikipedia.com (accessed Nov. 24, 2012) (34 pages).

\* cited by examiner a	b	c	d

METHOD FOR ISOLATING AND PURIFYING NUCLEIC ACIDS

The isolation of high-quality nucleic acids is a prerequisite for many different techniques in modern molecular biology, such as PCR amplification, blotting analysis and genomic-library construction, used for example in the field of molecular diagnostics. Especially if the nucleic acids are obtained from biological samples containing cellular material, it is necessary to separate them from contaminants like proteins, lipids and other cellular constituents that otherwise may interfere with restriction enzymes, ligases, and/or thermostable DNA polymerases used in these downstream applications. Furthermore, RNA nucleases (RNases) and particularly DNA nucleases (DNases) present in biological samples have to be removed to prevent degradation of the DNA.

A variety of different methods have been developed for the isolation of genomic DNA from biological samples containing cellular components. All of these methods involve a step of disrupting and lysing the starting material by breaking the cellular membrane and releasing its contents into solution. The mixture obtained is called lysate. In the following steps proteins, in particular nucleases, and the contaminants of the mixture and/or the used solutions are removed from the lysate, and finally the (more or less) purified DNA has to be recovered (an overview can be found in the QIAGEN brochure on "Genomic DNA Purification"). The step of purifying the DNA is of utmost importance, as carryover of mixture or buffer contaminants such as salts, detergents, organic solvents, in particular phenol and ethanol, often inhibit performance of DNA in downstream applications.

A very simple and fast technique for the isolation of genomic DNA from cell lysates is to incubate the cell lysates at high temperatures, e.g. at 90° C. for about 20 min or to directly use the lysates after an additional protease digestion. However, these lysates usually contain enzyme-inhibiting contaminants such as a high salt load, and accordingly these methods, which are considered as quick and dirty techniques, are only appropriate for a limited range of applications.

So-called salting-out methods, wherein proteins and other contaminants are precipitated from the crude cell lysate by adding a solution comprising a high concentration of a salt, such as potassium acetate or ammonium acetate, are well-known techniques for separating DNA from other cellular components present in a cell lysate. The precipitates formed are then removed from the solution comprising the DNA by centrifugation, and the DNA is recovered from the supernatant by precipitation with alcohol in a further step. In these methods, removal of proteins, in particular nucleases, and other contaminants often is quite inefficient, and an additional RNase treatment, a dialysis and/or repeated precipitations by alcohol are necessary to obtain DNA sufficiently pure to be used in downstream applications, which renders the methods tedious and time-consuming.

Another possibility to separate DNA from the other compounds present in a cell lysate is to extract the contaminants from the lysates using organic solvents. In a first step, the cells typically are lysed using a detergent, and the lysates are then extracted using solvents, such as phenol, chloroform, and isoamyl alcohol, to remove the contaminants. The toxicity of the solvents used is one drawback of these methods. Furthermore, special attention has to be paid to the pH and salt concentration to ensure that the majority of contaminants are extracted into the organic phase, while the DNA remains within the aqueous phase. The DNA is then recovered from the aqueous phase by alcohol precipitation. Even though organic extraction methods are very time-consuming, the DNA isolated using these methods often contains residual phenol and/or chloroform, which act as inhibitors in downstream applications such as PCR. In addition, toxic waste is generated which has to be disposed in accordance with hazardous waste guidelines.

In recent years sorption procedures based on ion exchange, affinity and/or hydrophobic interactions have been developed in order to minimize DNA degradation during purification. In these sorption procedures, the DNA is more or less specifically "sorbed", that is either adsorbed, absorbed or chemically bound, to a stationary solid phase, comprising a resin or a matrix, due to specific interactions between the DNA and the solid phase, while contaminants do not interact with the solid phase to the same extent as DNA does, and thus may be separated from the sorbed DNA, e.g. by a washing step. Once the contaminants have been removed, the DNA has to be recovered from the solid phase by an eluting step, which usually includes a step of rinsing the solid phase with a solution (mobile phase) comprising compounds that minimize the interaction between the solid phase and the DNA, thus removing the DNA from the solid phase. The mobile phase comprising the DNA (eluate) is then collected. These solid phase-based methods enable an automation of the process of DNA isolation and purification. In addition, also rather minute amounts of DNA can be reliably processed using these methods.

Anion-exchange methods are based on the interaction between the negatively charged phosphates of the nucleic acids and positively charged surface molecules on the anion-exchange carrier (Forcic et al., *J. Chromatogr. A* 2005, 1065 (1), 115-120). Under low-salt conditions DNA present in solution selectively binds to the stationary phase, and impurities such as RNA, cellular proteins, and metabolites may be washed away from the stationary phase using medium-salt buffers. In the next step, DNA can be eluted from the stationary phase using a buffer containing a high concentration of salt. The purified DNA is then recovered from the eluate by alcohol precipitation.

In silica-based methods, nucleic acids are selectively sorbed to a silica-gel membrane in the presence of high concentrations of chaotropic salts (Hanselle et al. *Leg Med (Tokyo)* 2003, 5 Supp. 1, 5145-5149). RNA, cellular proteins, and metabolites are washed away from the membrane, and the DNA is then eluted from the silica-gel membrane using a low-salt buffer.

Also solid-phase methods based on the interaction between DNA and magnetic particles as a stationary phase are known in the state of the art (Prodělalová et al. *J. Chromatogr. A* 2004, 1056, 43-48).

Even though sorption methods allow the isolation of high-quality DNA, the number of steps to be carried out in these "bind-wash-elute" routines still is comparatively high and thus time-consuming. For this reason a need exists for a method of isolating nucleic acids, preferably DNA and RNA, more preferred purified DNA, in particular genomic DNA, from biological samples, such as tissue and blood, wherein the number of steps to obtain the purified nucleic acids is reduced in comparison to the known sorption procedures, such as anion-exchange and silica-based methods, without compromising the purity of the nucleic acids obtained. Such a method should enable the user to reliably lyse biological samples, and to purify the nucleic acids present in the obtained lysate from contaminants such as proteins, in particular nucleases, lipids, and other cellular constituents. On the other hand the method should be gentle enough to minimize chemical or enzymatic degradation of the nucleic acids and mechanical shear stress, which otherwise would fragment the large genomic DNA during the course of purification. In addition, the method should be able to accommodate a wide variety of biological samples of different origin.

According to the present invention the term "nucleic acids" comprise any type or DNA or RNA as well as a mixture of DNA and RNA of any type.

A detailed analysis of the known methods for isolating and purifying DNA from cell-containing biological samples revealed that all these methods suffer from the fact that the DNA does not remain in solution during the whole procedure of isolating and purifying. Instead, the DNA either has to be precipitated or has to be bound, adsorbed or absorbed onto a solid matrix in the course of the isolation/purification procedure. In consequence, additional steps of redissolving the DNA from a precipitate or eluting it from a solid phase are necessary, which renders all of the methods mentioned above more or less time-consuming.

It was therefore an object of the present invention to provide a method for isolating and purifying nucleic acids, particularly comprising DNA from a cell-containing biological sample, wherein the number of steps required to isolate the nucleic acids, purified from contaminants such as proteins, in particular nucleases, and other cell components is reduced in comparison to the known methods, while still ensuring a high-quality DNA suitable for direct subsequent analysis by techniques such as PCR.

It has now surprisingly been found that high-quality nucleic acids, and in particular even high-quality purified DNA, preferred genomic DNA, can be obtained from a variety of biological samples by a method for isolating and purifying nucleic acids, preferably comprising genomic DNA, from a biological sample comprising at least DNA, RNA, and proteins, comprising the steps of: 1. mixing the sample with a lysis buffer comprising an anionic surfactant, but preferably being essentially free of a chelating or complexing agent, 2. incubating the mixture obtained in step 1 to obtain a lysate comprising at least DNA, RNA, and proteins, 3. optionally disintegrating the RNA present in the lysate, 4. precipitating the surfactant ions from the lysate preferably by adding to the lysate a solution comprising monovalent ions of alkali metals and/or divalent ions of alkaline earth metals preferably selected from the group comprising, preferably consisting of $Rb^+$, $Cs^+$, $Ca^{2+}$, $Sr^{2+}$, $Ba^{2+}$, or a mixture thereof, 5. separating the nucleic acids from the precipitate and further contaminants present in the lysate, wherein at least the further contaminants preferably are separated by size-exclusion chromatography. The precipitate may be removed by any other procedure than size exclusion or gelfiltration chromatography, but as well can be removed by said gel filtration chromatography together with the contaminants. In case the precipitate is removed by any other procedure, the liquid remainder (e.g. supernatant after centrifugation or eluate after filtration) is preferably further purified by gel filtration chromatography (size exclusion chromatography SEC), As an eluate from size exclusion chromatography the nucleic acids are obtained. The nucleic acids, particularly the DNA preferably remain essentially in solution during all of steps 2 to 5. Furthermore it is preferred that during the whole procedure no chelating or complexing agent is added to the sample. This means in particular that is preferred that none of the solutions added to the sample during the present procedure comprise a chelating or complexing agent.

Using the method of the present invention highly purified nucleic acids can be obtained, e.g. from tissue samples in about only 45 min (30 min lysis, 10 min of precipitation, 3 min pre-spinning of the column and 3 min for the chromatographic separation itself), while approximately 2.5 h typically are necessary for the lysis and purification of the same amount of tissue using e.g. the QIAamp kit (QIAGEN, Hilden, Germany). The method of the present invention provides in any case purified nucleic acids comprising DNA, purified from cellular contaminants. Particularly, dependent from the conditions and the steps used, either a mixture of DNA and RNA is obtainable or highly purified DNA can be prepared, which is as well separated from RNA. If in the following the term "DNA" is used, the DNA-containing purified nucleic acid sample is meant, either comprising RNA, or separated from RNA as well. Preferably the conditions of the method are resulting in a highly purified DNA, comprising essentially no RNA.

The quality and purity of the DNA isolated by the method of the present invention is equal, or in many cases even superior, to the quality and purity of DNA obtained by state of the art methods for bench-scale purification, such as for example the very successful QIAamp technology (QIAGEN, Hilden, Germany) with respect to purity and yield as judged by UVN is spectroscopy, gel electrophoresis, conductivity measurements, HPLC analysis, PCR and further assays. In addition, the DNA-containing eluate obtained by the method of the present invention may be frozen for longtime storage or may be processed in downstream applications like quantitative real time PCR (qRT-PCR), PCR and the like, immediately after chromatography without the need for any additional steps to isolate the DNA from the eluate. As the DNA remains essentially in solution during the purification process, and neither is precipitated by the addition of organic solvents such as for example ethanol, nor is sorbed or bound to a solid matrix such as a silica-membrane or an anion exchange resin, the method of the present invention is much faster than the methods for isolating and purifying DNA known from the state of the art. Furthermore, the method of the present invention can be fully automated.

Using the method of the present invention, in principle all kind of desoxyribonucleic acid (DNA) can be isolated from a wide variety of biological samples, including synthetic, genetically engineered or naturally occurring single-stranded or double-stranded DNA, oligo- and polynucleotides of desoxyribonucleotides, fragments of DNA obtained by partly digesting DNA using restriction endonucleases, mitochondrial DNA, plasmid DNA, and metagenomic DNA, representing the entirety of DNA obtained from all microorganisms found in a biotope or a biocenosis. Preferably the method of the present invention is used for isolating and purifying genomic DNA, which in terms of the present invention is the high molecular weight DNA obtained from one single organism, comprising the entirety of genetic information of this organism, in contrast to plasmid DNA, DNA partly digested by the action of restriction endonucleases, and metagenomic DNA. In this preferred embodiment, purified high molecular weight DNA is obtained, while smaller fragments of DNA are retained within the chromatographic material. Due to its high molecular weight and large size, intact high quality genomic DNA is difficult to isolate and purify, as a comparably high risk of degradation of genomic DNA exists, either by mechanical stress during the isolating procedure, in particular sheer stress, or by chemical and enzymatic degradation. Degraded DNA, on the other hand, may lead to both quantitative and qualitative errors in downstream analysis. The method of the present invention provides a fast, robust, safe, easy-to-handle and yet mild method for isolating and purifying DNA, in particular genomic DNA, from a variety of different biological samples.

For the method of isolating and purifying DNA according to the present invention, a lysis buffer was required which allows a fast lysis procedure under low-salt lysis conditions, as a high amount of salt in the lysate additionally complicates the purification process. In addition, it was necessary that also the other components of the lysis buffer do not interfere in any of the subsequent steps of the purification procedure according to the present invention or subsequent down-stream applications, or that potentially interfering components can be removed by a simple and fast purification step, while the DNA in the method of the invention remains essentially in solution.

It has surprisingly been found that a fast, yet mild lysis of biological samples can be achieved by using a new lysis buffer comprising an anionic surfactant providing a surfactant ion, preferably an anionic surfactant providing a source of sulfate ions, most preferably dodecyl sulfate ions ($DS^-$), but preferably being essentially free of a chelating or complexing agent. According to the present invention, a lysis buffer is an aqueous solution, comprising active components such as detergents, to disrupt and/or break the cellular membrane of a cell, causing the intracellular components, such as DNA, RNA, proteins, lipids, metabolites etc., to be released into solution. The solution comprising the former intracellular components is called lysate.

A further object of the present invention is therefore a lysis buffer comprising a buffering substance, $H_2SO_4$ and an anionic surfactant, wherein the buffer has a pH of 7.5 to 10, preferably of 8 to 9 and most preferably of 8.5 and is preferably essentially free of any chelating or complexing agent and $Mg^{2+}$-ions.

The buffer of the present invention allows a fast lysis of sample material under low-salt lysis conditions. In terms of the present invention, the term "low salt conditions" refers to hypotonic conditions, which means that the total ion concentration in the buffer solution is lower than the total ion concentration within the cells to be lysed. In the case of NaCl, for example, an aqueous solution comprising less than 0.9 wt % NaCl (about 155 mmol NaCl, corresponding to about 310 µmol/L of dissolved ions) is hypotonic. Even samples containing a rather high amount of solid material, for example tissue samples, are usually completely lysed within less than 40 min at e.g. 56° C. In principle, lysis can be carried out at temperatures ranging from 45° C. to 70° C., preferably from 50° C. to 68° C., and most preferred at 62° C. Since the lysis buffer of the present invention comprises a rather low amount of salt and preferably is essentially free of a chelating or complexing agent for the divalent ions necessary as co-factors for the polymerase in PCR reactions, and the pH of the lysis buffer falls within the optimum pH range for PCR reactions, the lysate obtained using the lysis buffer of the present invention can be directly used in downstream applications such as for example qRT-PCR. This is usually not possible using the lysis buffers known from the state of the art, which in general comprise EDTA, a chelating agent for divalent ions, such as $Mg^{2+}$ ions, necessary as co-factors of the polymerase enzymes necessary in PCR reactions.

Suitable anionic surfactants according to the present invention are e.g. sulfates, sulfonates and carboxylates, preferably alkyl sulfates (fatty alcohol sulfates), alkane sulfonates, alkylbenzene sulfonates and alkyl carboxylates. Particularly preferred are surfactants providing surfactant ions showing a similar precipitation behaviour as dodecyl sulfate ions ($DS^-$), more preferred are surfactants providing sulfate ions and most preferred are surfactants providing a source of dodecyl sulfate ions. As a source of dodecyl sulfate ions any compound releasing into solution dodecyl sulfate ions ($H_3C(CH_2)_{11}SO_4^-$) upon dissolution in water may be used. The source of dodecyl sulfate ions preferably is selected from the group comprising sodium dodecyl sulfate (SDS), ammonium dodecyl sulfate and lithium dodecyl sulfate, and most preferably is sodium dodecyl sulfate.

According to the present invention the lysis buffer preferably is essentially free of a chelating or complexing agent. Non-limiting examples for such agents are EDTA, EGTA, EDDS (ethylene diamine diacetic acid), NTA (nitrilo triacetic acid), gluconic acid, isoascorbic acid, tartaric acid, citric acid, iminodisuccinate, triethanolamine. In terms of the present invention a lysis buffer is essentially free of a chelating or complexing compound, e.g. EDTA, if it contains less than 10 mg/L, preferably less than 1 mg/L, more preferably less than 0.1 mg/L, even more preferably less than 0.001 mg/L, and most preferably the lysis buffer of the present invention does not contain any EDTA at all (0 mg/L).

In a preferred embodiment, the lysis buffer of the present invention is used in combination with a protease. A protease, sometimes referred to as proteinase, is an enzyme catalyzing the hydrolytic cleavage of the peptide bonds linking the amino acids in a polypeptide chain (protein). Suitable proteases are known from the state of the art and include QIAGEN Proteinase K or QIAGEN Protease, (QIAGEN, Hilden, Germany) without being limited to them. It has been found that the rather expensive Proteinase K may be replaced by the cheaper QIAGEN Protease without compromising the result of the purification procedure. The protease may already be present in the ready-to-use lysis buffer solution as supplied or may be added to the mixture by the user after mixing the biological sample with the lysis buffer.

The concentration of the anionic surfactant in the buffer depends on the sample to be lysed. The concentration of the source of surfactant ions, preferably the sulfate ions in the buffer preferably is 1 to 100 mmol/L, more preferably 5 to 75 mmol/L, even more preferably 10 to 50 mmol/L and most preferably 25 mmol/L.

The buffering substance can be any suitable buffering substance providing a pH of at least 7.5 like e.g. TRIS, HEPES, HPPS or any ammonia buffer. The preferred buffering substance is TRIS. The concentration of the buffering substance in the buffer preferably is in the range of 1 to 100 mmol/L, more preferably 5 to 75 mmol/L, even more preferably 10 to 50 mmol/L and most preferably 25 mmol/L.

The molecular ratio of the buffering substance, e.g. TRIS to the anionic surfactant, particularly to the source of sulfate ions in the buffer preferably is in the range of 3:1 to 1:3, more preferably 2:1 to 1:2, even more preferably 1.2:1 to 1:1.2 and most preferably is 1:1.

If samples comprising a high amount of liquid compounds such as blood are lysed, preferably a double concentrated buffer (2×) is used, wherein the concentration of each the anionic surfactant and the buffering substance is 2 to 200 mmol/L, more preferably 10 to 150 mmol/L, even more preferably 20 to 100 mmol/L, and most preferably 50 mmol/L, respectively, to avoid too high dilution of the mixture by the sample liquid. The lysis buffer may also be provided in form of a concentrate to be diluted by the user prior to use, comprising for example the ten-fold concentration of the anionic surfactant and the buffering substance (10× lysis buffer).

The lysis buffer of the present invention may comprise further active components selected from the group comprising stabilizers such as sodium azide, solubilizing agents or the like, which are well known to a person skilled in the art, even though the buffer composition of the present invention is stable at room temperature for more than eight months even in the absence of a stabilizer.

$H_2SO_4$ is used as acidic compound in the buffer composition due to the rather low solubility of sulfate salts, for example $SrSO_4$, in order to ensure an effective removal of any excess alkali or alkaline earth metal ions from the precipitating solution. The concentration of chloride ions in the buffer preferably is less than 10 mmol/L, more preferably less than 1 mmol/L, even more preferably less than 0.1 mmol/L.

The present invention further provides a method of lysing cells in a cell-containing biological sample comprising the steps of: 1. mixing the sample with a lysis buffer according to the present invention, 2. incubating the mixture obtained in step 1 to obtain a lysate comprising DNA, RNA and proteins. Preferably neither before nor during lysis any chelating or complexing agent is added to the sample.

According to the present invention, RNA present in the lysate may be optionally disintegrated after lysing the sample. In terms of the present invention the step of disintegrating RNA comprises any method of reducing the amount of dissolved RNA in the lysate and/or inactivating the RNA and/or facilitating its separation from the DNA, including any method of thermally, chemically and/or enzymatically hydrolyzing, digesting, transforming and/or decomposing RNA, either partially or completely, and/or removing the RNA or its fragments from the solution, e.g. by precipitation, sorption procedures or the like. A simple method for disintegrating the RNA in the sample is by heating the sample to a temperature of at least 60° C. without any further addition of an disintegrating agent. If the RNA shall remain in the sample heating of the sample only up to 58° C., preferably up to 56° C. is recommended. In a preferred embodiment for highly purified DNA, the step of incubating the mixture of the biological sample and the lysis buffer, and the optional step of disintegrating the RNA present in the lysate are carried out in a single step, preferably by heating the mixture to a temperature equal to or above 60° C., preferably to 60° C. to 70° C., more preferably to 61° C. to 65° C., and most preferably to 62° C. The period of time a sample has to be heated in order to ensure complete lysis and RNA disintegration depends on the kind and amount of sample being processed. Preferably the mixture is heated for 10 to 80 minutes (min), more preferably for 15 to 60 min, even more preferably for 20 to 50 min, and most preferably for 30 to 45 min.

Increasing the temperature during or after the lysis step up to 80° C. additionally denaturates the proteins (e.g. enzymes) in the sample without affecting the desired DNA, in particular genomic DNA. In this case of course RNA is not obtained.

The volume of lysis buffer used to lyse a certain amount of cell-containing sample material depends upon the kind and size of the sample material being processed. In the case of tissue samples it may for example be useful to cut large tissue sample into pieces of approximately 4 mm³ or less, before mixing the sample with the lysis buffer. Preferably a lysis buffer volume of 20 to 150 μL, more preferably of 30 to 120 μL, even more preferably of 50 to 100 μL and most preferably of 80 μL is used for the lysis of 10 mg of sample tissue. The amount of DNA obtainable from 10 mg of a sample using the method of the present invention depends upon the sample, for example its kind and age. Usually around 5 to 70 μg genomic DNA are obtained from 10 mg of different tissue samples using the method of the present invention.

Amounts of about 10 mg are the amount of sample commonly analyzed in molecular diagnostics. It should, however, be understood, that using the method of the present invention, it is also possible to process larger or smaller amounts of sample material, e.g. in the g-range or μg- to ng-range, respectively. In this case, the amounts of reagents, buffers, solid matrix as well as the dimension of the chromatographic device have to be adjusted by up- or down-scaling, which is well known to a person skilled in the art.

Using the method of the present invention cells from a wide variety of biological samples can be lysed and further processed in order to purify their nucleic acids, preferably genomic DNA, including, but not limited to, animal and human tissue, for example liver, spleen, lung, heart, brain, kidney etc., animal and human blood, cell cultures of animal and human cells, animal and human bone marrow, liquor, sputum or sperm, yeast, bacteria, insects, plants, and rodent tails. Preferably, the samples are cell-containing biological samples of animal or human origin. In another preferred embodiment, the samples comprise or consists of Gram-negative bacteria. The sample may be lysed immediately after being taken from its natural environment (fresh sample), or may be stabilized prior to lysis by freezing or by the action of chemical stabilizing agents, such as for example formalin-fixing and paraffin-embedding (FFPE tissue) or blood stabilizing agents comprising citrate or Heparin. Even more preferably the sample is selected from the group comprising fresh or frozen tissue and blood, most preferably from mammalian tissue and blood.

As already explained above, the lysis buffer preferably is essentially free of any complexing agent and its pH value falls within the optimum range for PCR reactions. Accordingly, the lysate obtained as described above may be directly used in a PCR reaction without further purification. In this case, dilution of the lysate is necessary due to the rather high concentration of the surfactant ions, e.g. the dodecyl sulfate ions in the lysate. As in preliminary experiments it has been found that concentrations of SDS above 312 μmol/L strongly inhibit PCR reactions, for the isolation and purification procedure of the present invention a method for selectively removing dodecyl sulfate ions from a sample comprising dodecyl sulfate ions and nucleic acids is highly preferred, wherein the nucleic acids, particularly the DNA remain essentially in solution.

For this reason, after lysing the sample and optionally disintegrating the RNA present in the lysate it is particularly preferred that surfactant ions like dodecyl sulfate ions are removed from the lysate in a further step, preferably by precipitation. Preferably a precipitating solution comprising monovalent ions of alkali metals and/or divalent ions of alkaline earth metals selected from the group comprising, preferably consisting of $Rb^+$, $Cs^+$, $Ca^{2+}$, $Sr^{2+}$, $Ba^{2+}$, or a mixture thereof, which form an insoluble precipitate with dodecyl sulfate ions, is added to the lysate, as described in the co-pending application with the title "method for precipitating anionic surfactant ions in the presence of nucleic acids" of the same applicant having the same filing date as the present application. In a preferred embodiment the precipitating solution comprises alkali earth metal ions, in a particular preferred embodiment, the precipitating solution comprises $Sr^{2+}$-ions. In terms of the present invention the term precipitating is understood as a step of adding to a solution, comprising dissolved DNA and dodecyl sulfate ions, a substance or a mixture of substances that interact or react with the dodecyl sulfate ions to form a compound being insoluble in the resulting solution, thus precipitating from the solution. Preferably the DNA remains essentially in solution during this step. The DNA is then separated from the precipitate and from further contaminants which may be present in the lysate, wherein at least the further contaminants are separated preferably by size-exclusion chromatography to obtain a purified DNA-containing eluate The precipitate may be removed by any other procedure than size-exclusion or gelfiltration chromatography, but as well can be removed by said gel filtration chromatography together with the contaminants. In case the precipitate is removed by any other procedure, the liquid remainder (e.g. supernatant after centrifugation or eluate after filtration) is further preferably purified by gel filtration chromatography (SEC), As an eluate from said size exclusion chromatography the nucleic acids are obtained. The precipitate comprising the solid material, formed from the interaction of surfactant ions, e.g. the dodecyl sulfate ions and the ions of alkali metals or alkaline earth metals, and further solid material, being insoluble in the lysis buffer, is removed before or in the gel filtration step, such as complexed surfactant ions or derivatives thereof, and proteins, precipitated proteins and the like. A further advantage of the present invention is that due to the use of size-exclusion chromatography for purifying the DNA-containing solution not only solid material is separated from the dissolved DNA, but also dissolved contaminants such as proteins, optionally residual fragments of RNA, metabolites, lipids and other components typically being present in biological samples.

The step of selectively precipitating the surfactant ions, preferably the dodecyl sulfate ions is preferably carried out by: 1. Adding to the liquid sample a solution (precipitating solution), comprising monovalent ions of alkali metals and/or divalent ions of alkaline earth metals selected from the group comprising, preferably consisting of $Rb^+$, $Cs^+$, $Ca^{2+}$, $Sr^{2+}$ and $Ba^{2+}$, or a mixture thereof, and 2. optionally incubating the mixture comprising the liquid sample and the precipitating solution to ensure completeness of precipitate formation as described in co-pending application with the title "method for precipitating anionic surfactant ions in the presence of nucleic acids" of the same applicant having the same filing date as the present application. In a preferred embodiment the precipitating solution comprises divalent ions of alkaline earth metals, in a particular preferred embodiment $Sr^{2+}$-ions.

The precipitating solution preferably comprises a water-soluble salt of alkali metals and/or alkaline earth metals, like for example RbCl, $SrCl_2$, $CaCl_2$ or $BaCl_2$ which upon dissolution in water provides monovalent ions of alkali metals and/or divalent ions of alkaline earth metals. These ions form a compound with the surfactant ions, particularly preferred with the dodecyl sulfate ions being insoluble in water, in aqueous solutions of neutral or alkaline pH, or in aqueous buffers, which results in precipitate formation, thus removing the dissolved surfactant ions from the solution. The concentration of the monovalent and divalent metal ions in the precipitating solution preferable is in the range of 0.1 to 10 mol/L, preferably of 0.5 to 5 mol/L, more preferably of 0.75 to 2.5 mol/L, and most preferably of 0.9 to 1.2 mol/L. Such a rather high concentration of said ions in the precipitating solution is preferred in order to allow addition of a small volume and accordingly to avoid a too high dilution of the sample solution.

The volume of precipitating solution added to a certain volume of sample solution (lysate) depends upon the concentration of the surfactant ions in the sample solution. In a preferred embodiment, the volume ratio of sample solution to precipitating solution is in the range of 4:1 to 12:1, preferably 5:1 to 11:1, more preferably 6:1 to 10:1 and most preferably 7:1 to 9:1. If for example 80 µL of sample solution are obtained by lysing a sample according to the present invention, then preferably 10 µL of a 1 M precipitating solution is added to precipitate the surfactant ions like dodecyl sulfate ions.

In a further preferred embodiment, the mixture is incubated at −10° C. to 10° C., preferably at −5° C. to 5° C., more preferably at −2.5° C. to 2.5° C. and most preferably at −1° C. to 1° C. The lower the incubation temperature, the faster precipitation is completed. However, the incubation temperature should be above the freezing point of the mixture to avoid a solidification of the whole mixture. The freezing point of a particular sample mixture depends upon the amount of salt dissolved in that mixture which is well known to a person skilled in the art, and the incubation temperature will be chosen accordingly. The step of incubating preferably is carried out for 3 to 60 min, preferably for 5 to 30 min and most preferably for about 10 min. Preferably the mixture is left to stand for the time given in an ice bath, which ensures completeness of precipitate formation. In a preferred embodiment, the precipitate formed may then be removed by filtration, preferably by gel filtration chromatography.

For the step of separating DNA from the precipitate and further contaminants present in the lysate, preferably a chromatographic device for purifying DNA, preferably genomic DNA, from contaminants by gel filtration chromatography as described in co-pending application with the title "chromatographic device and method for isolating and purifying nucleic acids" of the same applicant having the same filing date as the present application is used, comprising at least one chromatographic unit, comprising: 1. A hollow body having an inlet and an outlet, the hollow body comprising a solid matrix providing size excluding properties, preferably forming a gel bed; 2. a porous frit, filter, fleece or membrane preferably allowing nucleic acids of any size to pass, placed between the outlet and the solid matrix to retain the solid matrix within the chromatographic unit, 3. a non-porous ring placed between the porous frit, filter, fleece or membrane and the matrix, sealing the outer area of the frit, filter, fleece or membrane, to prevent the mobile phase from entering the frit without passing the matrix, 4. optionally at least one removable closing device to seal the inlet and/or outlet of the chromatographic unit, and 5. optionally at least one collection tube to collect the mobile phase (eluate) after having passed the matrix, wherein the solid matrix in a preferred embodiment is a gel forming polymer having a size exclusion limit of 150 to 500 base pairs (bp), preferably 200 to 400 bp, and most preferably 250 to 300 bp. Preferably the gel forming polymer has a corresponding size exclusion limit of 10 to 10000 KDa, more preferred of 20 to 8000 kDa.

Using this device, a "negative" chromatography is possible, where in contrast to the other chromatographic methods commonly used for the chromatographic purification of DNA, not DNA, but the contaminants are sorbed to the solid matrix, thus allowing the chromatographic purification to be carried out in one single rinsing step. Accordingly, the step may be referred to as a "single-step" chromatography. Such chromatographic devices are able not only to remove contaminants of small molecular weight, but also act as a depth filter for solid material, in particular the precipitate formed from dodecyl sulfate ions and the monovalent alkali metal ions or divalent alkaline earth metal ions. Said precipitate does not enter the gel bed, but remains on its upper surface. This is even more surprising, since solid material usually tends to clock the pores of a gel, thus hampering or disturbing further chromatography. Using the chromatographic device described in co-pending application with the title "chromatographic device and method for isolating and purifying nucleic acids" of the same applicant having the same filing date as the present application in combination with the method of the present invention, a lysate containing highly purified de-salted DNA, in particular gDNA, essentially free from residual dodecylsulfate ions can be obtained.

The chromatographic device preferably is used for size exclusion chromatography (SEC). In the present invention, preferably a water-based mobile phase, such as water, an aqueous organic solvent or an aqueous buffer/solution, is used as mobile phase. In this case SEC is also referred to as gel filtration chromatography. Size exclusion chromatography is a chromatographic method, wherein molecules are separated based on their size, or more precisely based on their hydrodynamic volume. Commonly, a solid matrix able to form a gel bed, when suspended in an aqueous medium, such as a dextran, agarose, polyacrylamide, or a mixture thereof, is suspended in a buffer and packed in the hollow body of a column made of glass, plastic, Teflon or any other material that neither reacts with the mobile phase nor the analyte. The sample to be purified is then applied to the center of the gel bed's upper surface, and allowed to pass through the gel, either by gravity or forced by centrifugation or pressure. According to the present invention preferably centrifugal forces are applied to move the mobile phase down the column, wherein the columns are spun in a centrifuge (so-called spin column technique). Due to the cross-linking in the gel, pores of a certain size exist inside the gel. Small molecules are able to penetrate the pores, and therefore move through the gel bed more slowly, being retained as they pass down the column, while large molecules cannot penetrate the pores and move down the column more quickly. After having passed the column, the mobile phase (now referred to as eluate), containing the purified analyte, is then collected at the outlet of the column. To retain the solid matrix within the hollow body of the column, a porous frit, filter, fleece or membrane is preferably placed between the outlet of the column and the solid matrix.

In SEC, the size exclusion limit defines the molecular weight, where molecules are too large to be trapped in the stationary phase. The size exclusion limit of a solid matrix can be adjusted by the degree of cross-linking in the gel. A wide variety of solid matrices able to form a gel bed with different degrees of cross-linking are commercially available.

A problem often encountered in gel filtration chromatography, and particular in gel filtration chromatography using spin columns, is that the mobile phase may run down along the inner wall of the column, thus entering the frit without having passed the solid matrix. This is especially true for high-throughput applications, when not all of the sample solution to be purified is applied exactly to the center of the gel bed's flat surface, or the sample is applied to quickly. When the mobile phase does not enter the gel bed, no chromatographic separation occurs, and a contaminated eluate is obtained. To overcome this problem, the chromatographic device preferably used in the present invention is equipped with a non-porous ring placed between the porous frit, filter, fleece or membrane and the matrix. This ring seals the outer area of the frit, filter, fleece or membrane, thus preventing the mobile phase from entering the frit without having passed the matrix. In addition, the velocity of the mobile phase inside the column is slowed down, thus improving selectivity.

The optional chromatographic device may contain removable closing devices to seal the inlet and the outlet of the chromatographic unit, and the solid matrix is preferably supplied in the form of a gel, pre-swollen in a solvent selected from the group comprising water, the homogenous mixtures of organic solvents with water, or aqueous buffers. In this case, the solvent is preferably purged from the chromatographic unit, while simultaneously establishing the matrix bed by centrifugation immediately prior to use (pre-spinning).

The gel-forming polymer preferably is selected from the group of comprising dextrans, agarose, polyacrylamide, or mixtures thereof, and more preferably is a mixture of a dextran and a polyacrylamide. Such gel-forming polymers of different size exclusion limits are commercially available, for example under the trademark name of Sephacryl, Sephadex, or Sepharose. A particular preferred solid matrix is the S-400 HR Sephacryl resin, commercially available from GE-Healthcare, which is a spherical allyldextran/N,N'-methylene bisacrylamide matrix with a size exclusion limit of 271 bp (corresponding to 20-8000 kDa). Further suitable gel-forming polymers may have a methacrylic basis, like a hydroxylated methacrylic polymer, for example HW 65 available from Tosoh Bioscience LLP (former TosoHaas) with a size exclusion limit of 5.000 kDa.

By using a chromatographic device comprising a plurality of chromatographic units in a parallel fashion, e.g. in the form of a multiwell plate wherein each well of the multiwell plate contains one separate chromatographic unit, parallel high through-put processing of a multitude of different samples is possible using the method of the present invention.

The step of separating the DNA from the precipitate and further contaminants present in the lysate by size-exclusion chromatography to obtain a purified DNA-containing eluate according to the present invention preferably comprises the steps of: 1. establishing the matrix bed in the chromatographic unit by centrifugation (pre-spinning), 2. applying the lysate to (the center of) the matrix bed upper surface, 3. eluting the DNA from the chromatographic unit by centrifugation and simultaneously collecting the eluate. It is particularly preferred that no further step has to be carried out between step 2 and 3, in particular no washing steps. Since the desired DNA doesn't bind to the gelforming polymer of the matrix but elutes, step 3 can be immediately carried out after step 2.

The volume of the matrix bed in the chromatographic unit preferably is in the range of 100 µL to 2 mL, more preferably in the range of 500 µL to 1 mL, and most preferably is 700 to 800 µL. The filling level of the matrix bed in the chromatographic unit preferably is in the range of 0.5 cm to 2.0 cm, more preferably 1.0 to 1.5 cm. In a standard 96-well plate the volume of the matrix bed preferably is about 0.8 mL. The matrix is preferably provided as a dispersion of the gel-forming polymer in water, a salt solution, e.g. 0.9% NaCl, or a suitable buffer, like e.g. TE, TAE, PBS or similar or in diluted buffers, whereas said dispersion comprises preferably 60-90%, more preferably 70-80% and in particular 75% of the gel-forming polymer. The exact volume and the filling level of matrix bed used depend on the size and shape of the hollow body defined by the column, as well as on the kind and amount of the sample to be purified, which is well known to a person skilled in the art. Preferably a sample volume of up to 100 µL is applied to a column packed with 600 µL to 800 µl or a filling level of 1.0 cm to 1.5 cm of matrix bed.

Herein pre-spinning preferably is carried out by centrifuging the device at 500 to 900×g for 1 to 7 min, preferably at 700×g for 2 to 5 min, and most preferably at 700×g for 3 min.

Eluting the DNA from the chromatographic unit preferably is carried out by centrifuging the device at 500 to 900×g for 1 to 7 min, preferably at 700×g for 2 to 5 min, and most preferably at 700×g for 3 min. Preferably the time and centrifugation force which is applied should correspond to the time and force used for pre-spinning (see above).

The invention further provides a kit for the isolation and purification of nucleic acids, preferably comprising DNA, more preferably for isolation of highly purified DNA, preferably genomic DNA, comprising: 1. A lysis buffer according to the present invention, 2. a source of monovalent ions of alkali metal and/or divalent ions of alkaline earth metal selected from the group comprising, preferably consisting of $Rb^+$, $Cs^{2+}$, $Ca^{2+}$, $Sr^{2+}$, $Ba^{2+}$ or mixtures thereof, either in the form of a water-soluble alkaline earth metal salts to be dissolved by the user, or as a stock solution to be diluted by the user, or as a ready to use solution, 3. optionally a chromatographic device for purifying nucleic acids, preferably genomic DNA, from contaminants by gel filtration chromatography, comprising at least one chromatographic unit comprising (1) a hollow body having an inlet and an outlet, the hollow body comprising a solid matrix providing size excluding properties, preferably forming a gel bed, (2) a porous frit, filter, fleece or membrane, placed between the outlet and the solid matrix, to retain the solid matrix within the chromatographic unit, (3) a non-porous ring, placed between the porous frit, filter, fleece or membrane and the matrix, sealing the outer area of the frit, filter, fleece or membrane, to prevent the mobile phase from entering the frit without passing the matrix, (4) optionally at least one removable closing device to seal the inlet and/or outlet of the chromatographic unit, and (5) optionally at least one collection tube to collect the mobile phase (eluate) after having passed the matrix, wherein the solid matrix preferably is a gel-forming polymer having a size exclusion limit of 150 to 500 bp, preferably 200 to 400 bp, and most preferably 250 to 300 bp, and 4. optionally one or more primers for the direct amplification of one or more target nucleic acids from the eluate. Further, preferably instructions for using the content of the kit to carry out the present procedure are obtained.

EXAMPLES

Materials and General Experimental Procedures

Figure 1:
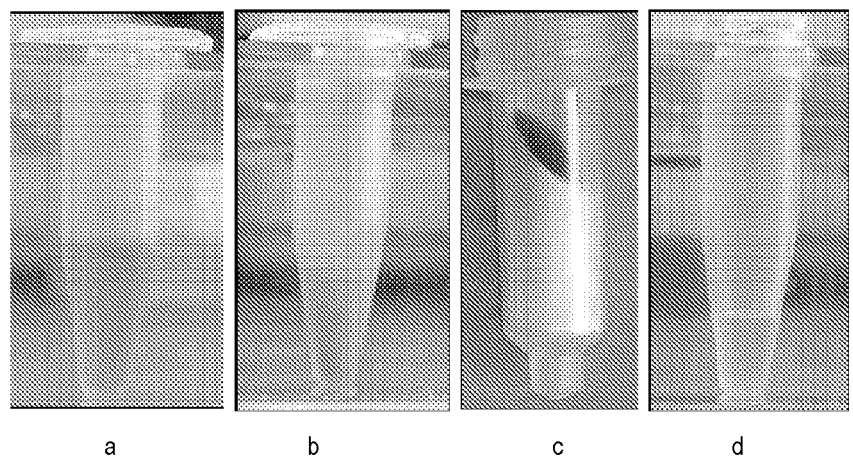
FIG. 1 depicts the DNA purification process of the present invention from the tissue lysate (a), which then is mixed with the precipitating solution (b), and purified by gel filtration chromatography (the used spin column is shown in (c)) to obtain an eluate (d) (from left to right).

Gel filtration media were obtained from GE-Healthcare (Freiburg, Germany), ion-exchange media were obtained from Merck KgaA (Darmstadt, Germany).

Unless otherwise noted, the tissue samples analyzed were rat liver tissue samples.

Determination of the amount and purity of gDNA: To estimate the amount of gDNA (gDNA yield) in a purified sample (eluate), the absorbance of the sample was measured at a wavelength of 260 nm by UV/Vis spectroscopy. A background absorption value, measured at 320 nm was subtracted from the $OD_{260}$ value (optical density at 260 nm), and the value was multiplied by 50, the specific absorbance factor of DNA, and by the dilution factor to obtain the gDNA concentration in µg/µL. In addition, UV/Vis spectroscopy was also used to judge the purity of the DNA obtained. Residual solid particles do not exhibit a distinct absorbance peak, but lead to an elevated baseline in the whole spectrum. Free haemoglobin has an absorbance maximum at a wavelength of 410 nm, while salts and preservatives like sodium azide absorb at a wavelength below 230 nm. A Spectramax II (Molecular Devices, Sunnyvale, Calif., USA) 96-well plate photometer was used to record the UV/Vis spectra.

A more precise determination of the amount of gDNA obtained was carried out using HPLC analysis. The area under curve (AUC) for the gDNA-containing peaks in the spectra was calculated by the software and compared to a HPLC standard curve, to determine the amount of gDNA in a sample. HPLC analysis was also used to determine the purity of the samples using a Vision BioCad workstation (Perseptive Biosystems, Framingham, Mass., USA). A 0.83 mL Peek column filled with the ion exchange resin TMAE-Fractogel (S) (E. Merck, Darmstadt, Germany) was used. The samples were analyzed at a flow rate of 1.5 mL/min in an increasing $CaCl_2$ gradient, starting from 0 mmol/L to 300 mmol/L over a period of 35 column volumes, buffered at pH 7.2. The absorbance was continuously monitored at 260 nm and 410 nm.

Agarose gel electrophoresis was carried out using a 50 mL 0.8% agarose gel, containing 2.5 µL SYBR-Green II. Samples were run using a voltage of 100 Volt for a time period of 40 min. The gels were analyzed using commercially available equipment from BioRad or LTF-Labortechnik (Wasserburg, Germany).

SDS quantification: The residual SDS concentration was determined by UV/Vis spectroscopy according to a modified procedure of Rusconi et al. adapted to be used within a 96 well photometer (Rusconi et al. *Anal. Biochem.*, 2001, 295(1), 31-37). The assay is based on a specific reaction of the carbocyanine dye "Stains All" (4,5,4',5-Dibenzo-3,3'-diethyl-9-methylthiocarbocyanine bromide) with SDS, which leads to the formation of a yellow colour (absorbance maximum at 438 nm). As SDS was used as the source of dodecyl sulfate ions in the present examples, it should be understood that the amount (molarity) of SDS in a solution equals the amount (molarity) of dodecyl sulfate ions present in solution.

1 mL of a stock solution of the dye (1.0 mg "Stains All" in 1.0 mL 50% isopropanol) was diluted with 1.0 mL formamide and 18 mL water to obtain a ready-to-use solution of the dye. To determine the amount of SDS in a sample, 5 µL of the sample solution were placed into a microtiter plate, mixed with 100 µL of the ready-to-use solution, and incubated at room temperature for 5 min in the dark before reading the plate at 438 nm. The amount of SDS in the sample was retrieved by comparison with a calibration curve, established by recording the absorbance of solutions containing a SDS concentration of 250, 167, 111, 74, 49, 32 and 21 µmol/L, respectively, at 438 nm.

Conductivity measurement: To determine the ion strength in the samples, conductivity measurements were carried out using a Consort C831 Conductometer (LTF-Labortechnik, Wasserburg, Germany), calibrated to 20° C. A minimum volume of 2 mL is necessary for the measurement, therefore aliquots of 20 µL of each sample were diluted with 1980 µL water prior to the measurement.

PCR amplifications: Real time-PCR (qRT-PCR) assays were performed on a Rotor-Gene 2000 or 3000 cycler (Corbett, Sydney, Australia) on a 50 µL scale, or in a TaqMan 7700 analyzer (Applied Biosystems, Foster City, Caif., USA).

For the jun RT-PCR assay, a commercially available kit (Part. No: 4327113F), based on a primer/probe system (FAM) from Applied Biosystems (Darmstadt, Germany), including a 20× Jun PCR primer/probe mix was used in combination with a 2× TaqMan PCR universal master mix from Applied Biosystems.

A genomic DNA standard was purified from rat tail using the QIAsymphony DNA kit on QIA-symphony platform (QIAGEN, Hilden, Germany), and was further purified by subsequent anion exchange chromatography (AEX) using a QIAGEN tip 2500 according to the manufacturers' protocol (QIAGEN, Hilden, Germany). The gDNA was stored in aliquots at −20° C. and thawed immediately prior to use.

Example 1

Lysis of Pork Liver Tissue with Different Buffers, Different pH

Lysis buffers of the following compositions were prepared: reference buffer A: 100 mmol/L TRIS, 5 mmol/L EDTA, 100 mmol/L $MgSO_4$ and 100 mmol/L SDS, adjusted to pH 6.0 by the addition of $H_2SO_4$; reference buffer B: 100 mmol/L TRIS, 5 mmol/L EDTA, 100 mmol/L $MgSO_4$ and 100 mmol/L SDS, adjusted to pH 8.0 by the addition of $H_2SO_4$; lysis buffer according to the present invention: TRIS 25 mmol/L, SDS 25 mmol/L, adjusted to pH 8.5 by the addition of $H_2SO_4$ (25% v/v). All buffer compositions were prepared as aqueous solutions. Reference buffer compositions A and B are based on standard buffer compositions, commonly used for lysing cell-containing material, additionally containing $Mg^{2+}$-ions, which were reported to degrade RNA at alkaline pH and temperatures above 37° C. (N. G. AbouHaidar and I. G. Ivanov *Z. Naturforsch.* 1999, 54 c, 542-548). Samples of pork liver tissue (25 mg each) were incubated with 500 µL of reference buffer A, reference buffer B and the buffer according to the present invention, respectively, at 56° C. To aid depletion of proteins 10 µL of QIAGEN Proteinase K (2.5 AU/ml) (QIAGEN, Hilden, Germany) was added to each sample solution. While lysis of the pork liver tissue was usually complete within 40 min using reference buffer B and the buffer of the present invention, residual tissue fragments were still present even after two hours of incubation when using reference buffer A. Thus, the results described by Abou-Haidar et al. could not be verified.

Reference Example 2

Precipitation of Dodecyl Sulfate Ions from the Lysate Obtained Using Reference Buffer B Although it was known from the state of the art that potassium salts of dodecyl sulfate have a very low solubility at acidic or almost neutral pH, it was initially attempted to precipitate the dodecyl sulfate ions in the lysate obtained using reference buffer B by the addition of potassium ions. With the intention to directly use the lysates in a PCR reaction, after precipitation of dodecyl sulfate ions, and subsequent removal of the precipitate formed, solutions of alkaline potassium salts were added to the lysate in order to precipitate dodecyl sulfate ions, as PCR reactions usually require a pH of about 8 to 9.

For this reason potassium carbonate ($K_2CO_3$) and potassium bicarbonate ($KHCO_3$) were tested as an alkaline source of potassium ions. Samples of 20 mg of pork liver tissue were suspended in 500 µL of reference buffer B (pH 8.0) and incubated at 56° C. for 30 min. To precipitate the dodecyl sulfate ions from the lysate, 140 µL of a 0.25 M aqueous solution of $K_2CO_3$ per sample and 350 µL of a 0.25 M aqueous solution of $KHCO_3$ per sample were added to two samples, respectively. All samples were incubated in an ice bath for 5 min. While the addition of KHCO3 did not alter the pH of the lysate significantly, a slight increase of pH was observed after addition of $K_2CO_3$. For this reason samples treated with $K_2CO_3$ were neutralized by adding 3 µL 2% HCl (aq). All samples were centrifuged to remove the precipitate, and aliquots of the supernatants (4 µL) were analyzed on an agarose gel. As a positive control DNA from two further samples of pork liver tissue lysed using reference buffer B was purified on a QIAsymphony platform (QIAGEN, Hilden, Germany) according to the QIAsymphony DNA handbook May 2008, using a bind-wash-elute concept based on magnetic particles including a RNAse treatment.

Figure 2:
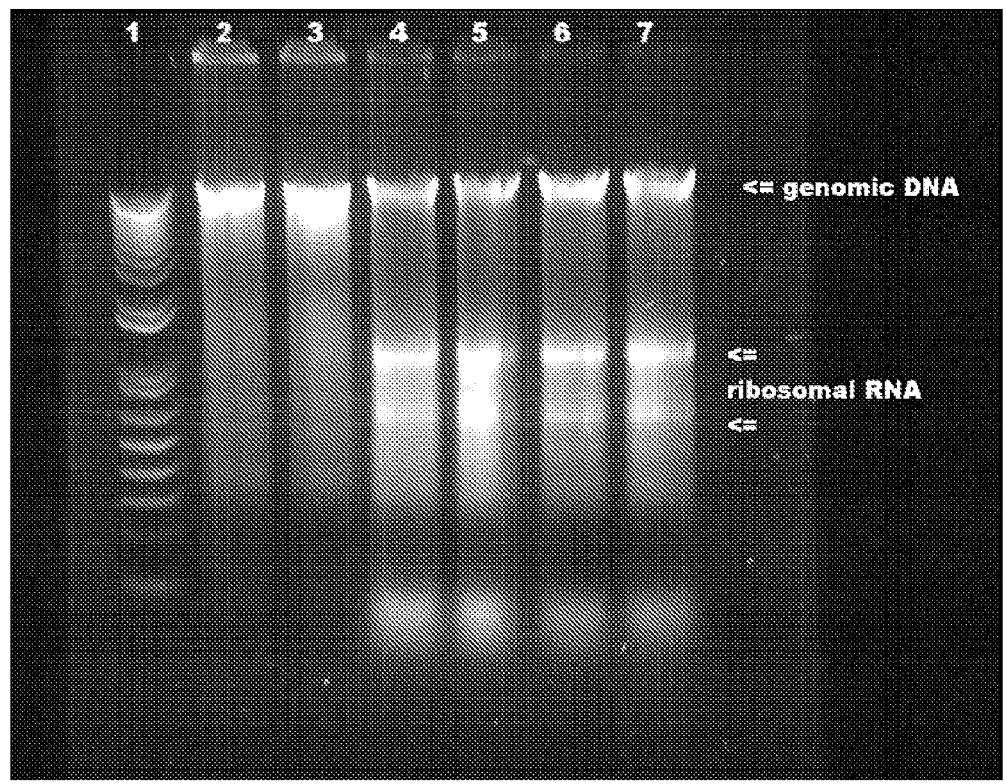
FIG. 2 shows a SYBR-Green II stained agarose gel obtained by gel electrophoresis of pork liver tissue samples, lysed with a buffer comprising TRIS, SDS, EDTA and $MgCl_2$ according to reference example 2. A DNA size standard is shown in lane 1. The samples analyzed in lanes 2 and 3 have been purified using the QIAsymphony platform (QIAGEN, Hilden), while in samples shown in lanes 4 and 5 as well as 6 and 7, dodecyl sulfate ions were removed by the addition of $K_2CO_3$ and $KHCO_3$, respectively. A large amount of ribosomal RNA (rRNA) is present in all the samples treated with potassium ions.

The electrophoresis gel is shown in FIG. 2. The Gibco 1 kb Plus DNA Ladder (Invitrogen GmbH, Karlsruhe, Germany)) was used as a length standard to identify the size of fragments present in the samples (lane 1). In lanes 2 and 3, lysates purified using the QIAsymphony platform were analyzed. In these samples mainly gDNA of a decent quality is detected, while a large amount of ribosomal RNA (rRNA) is present in the samples treated with $K_2CO_3$ (lanes 4 and 5) and $KHCO_3$ (lanes 6 and 7). The presence of rRNA in the samples was unexpected, since it should have been hydrolyzed by the combination of a TRIS buffer and magnesium ions within a lysis time of 30 min at pH 8.0 according to AbouHaidar.

The lysis experiment was therefore repeated using different concentrations of reference buffer B, ranging from a 0.25-fold concentration to 2-fold concentration with an increased incubation time of 40 min at 56° C. Regardless of the buffer concentration, intact RNA was detected in the SYBR-green II stained agarose gel of all samples (data not shown). Accordingly, a combination of magnesium ions with a TRIS buffer additionally containing SDS at a slightly alkaline pH cannot be used for the disintegration of RNA from lysed tissue samples in the presence of intact genomic DNA.

Example 3

Disintegration of RNA at Various Temperatures in the Absence of Magnesium Ions To study the effect of temperature on the lysis of tissue samples and on the disintegration of RNA present in the lysates obtained, samples of 10 mg pork liver were suspended in a buffer containing 25 mmol/L TRIS and 25 mmol/L SDS, but no EDTA and no $MgCl_2$, adjusted to pH 8.0 by the addition of $H_2SO_4$. The samples were incubated at different temperatures for 40 min, and subsequently analyzed by gel electrophoresis.

Figure 3:
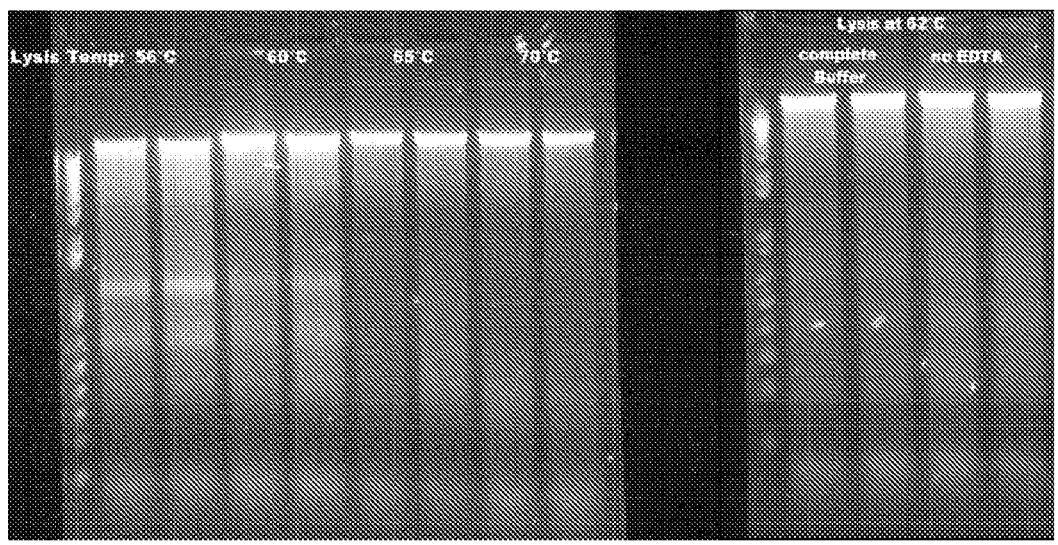
FIG. 3 is a picture of an agarose gel obtained from lysates of 10 mg pork liver tissue after having been incubated at different temperatures for 40 min (see Example 3). While in the sample incubated at 56° C. RNA still is clearly visible, disintegration of RNA is possible by increasing the incubation temperature. The picture on the right hand side furthermore shows, that the integrity of the gDNA is not compromised, when no EDTA is present in the lysis buffer (see Example 3).

The results are presented in FIG. 3: while a large amount of RNA still is present after incubating the samples at 56° C., the amount of RNA is significantly reduced after incubating the samples at 60° C. When the samples are incubated at temperatures above 60° C., no RNA can be detected by gel electrophoresis. The optimum temperature was determined to 62° C. Furthermore, it is possible to omit EDTA from the lysis buffer without compromising the integrity of gDNA as shown in the agarose gel on the right hand side, which enables a subsequent PCR reaction without the need for removing the chelating agent.

Figure 4:
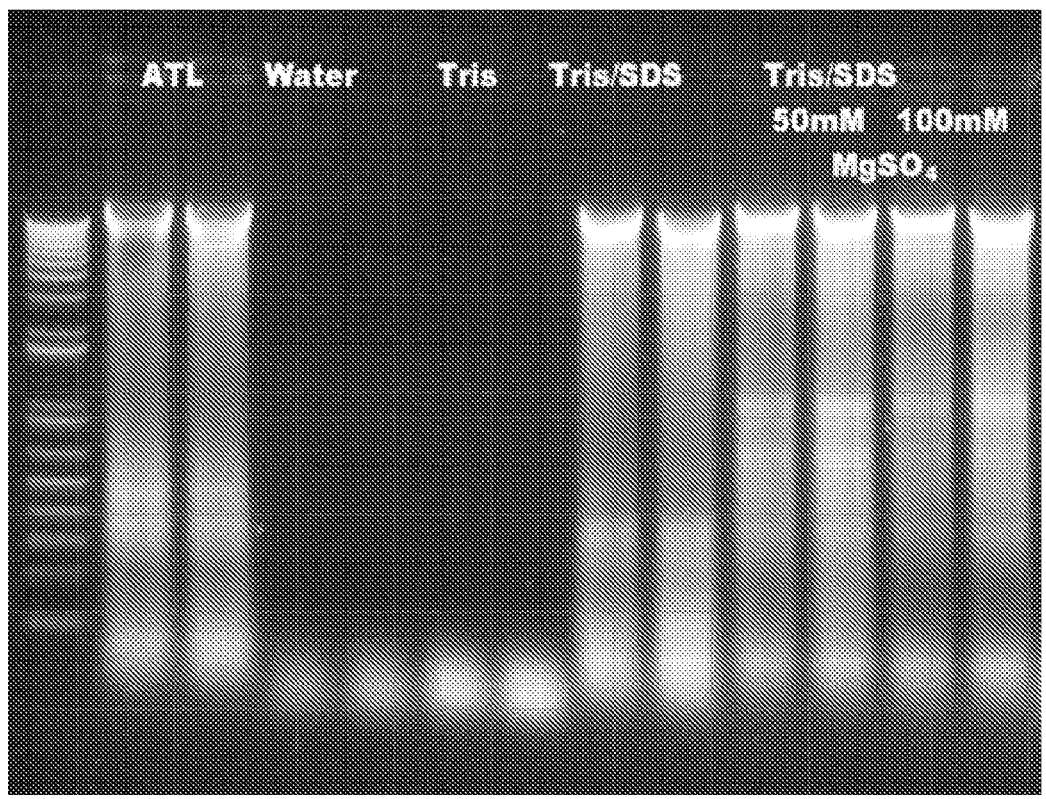
FIG. 4 shows an agarose gel analysis of lysates of 10 mg liver tissue, after having been incubated for 30 min at 62° C. in different buffers or aqueous solutions (see Example 3).

In a further experiment, samples of 10 mg liver tissue were subjected to lysis by incubating the samples in different solutions/buffers at 62° C. for 30 min. Each experiment was carried out in duplicate. The results are presented in FIG. 4: In water as well as in an aqueous solution of 25 mmol/L TRIS, not comprising SDS, no detectable gDNA was observed. In commercially available QIAGEN ATL buffer (QIAGEN, Hilden, Germany) as well as in a buffer according to the present invention, comprising TRIS and SDS, complete disintegration of RNA was observed, while the gDNA present in the sample is protected from hydrolysis. Addition of $MgSO_4$ (50 mM or 100 mM, respectively) to TRIS/SDS buffer results in that RNA is protected from hydrolysis even at a temperature of 62° C. Thus, the optimum buffer composition should comprise TRIS and SDS, both at a concentration of 25 mmol/L, the pH of the buffer solution being adjusted to pH 8.5 by the addition of sulfuric acid, but should be free of $Mg^{2+}$-ions and EDTA. A protease such as QIAGEN Protease or QIAGEN Proteinase K (10 µL; 2.5 AU/ml) may be added to the buffer, preferably after resuspension of the tissue material to aid disintegration of proteins.

Example 4

Optimization of the Spin Column Used for the Purification of gDNA from the Lysate As described in copending application with the title "method for precipitating anionic surfactant ions in the presence of nucleic acids" of the same applicant having the same filing date as the present application, it has been found that strontium chloride is also effective in precipitating residual proteins and that the concentration of $SrCl_2$ in the precipitating solution should be adjusted to 1.0 M to ensure a low sample dilution by the precipitating solution. 10 µL of this 1 M precipitating solution are sufficient to effect precipitation of dodecyl sulfate ions and residual proteins from lysates obtained by incubating 10 mg of tissue in 80 µL of the lysis buffer according to the present invention. To ensure completeness of precipitate formation, it is advantageous to incubate the samples in an ice bath before applying them to filtration devices. It has further been found that filtration is more effective in removing the precipitate formed from dodecyl sulfate ions and $Sr^{2+}$-ions and that the minimum amount of resin necessary to ensure homogenous gel bed formation in a spin column having a column height of 2.5 cm, and an inner diameter of 0.8 to 0.9 cm, is 600 µL. Further, a problem commonly observed in gel filtration chromatography using spin columns, i.e. the fact, that lysate may run down the inner walls of the spin column passing the frit without having entered the gel bed has been solved by introducing a non-porous ring, placed between the porous frit, filter, fleece or membrane and the matrix, sealing the outer area of the frit, filter, fleece or membrane, to prevent the mobile phase from entering the frit without passing the matrix.

The optimum size exclusion limit of the matrix bed was then determined. 600 μL of different commercially available gel filtration matrices (Sephacryl resins comprising a matrix of spherical allyl dextran and N,N'-methylene bis-acrylamide) were filled into a spin column as shown in FIG. 1, equipped with a dense silica frit (Mat. No. 1017499, QIAGEN, Hilden, Germany), a plastic ring, and a screw cap. The size exclusion limits of the resins used (in base pairs, bp, or in kDa, respectively, as far as provided) are given in table 1.

TABLE 1

| Resin | Size exclusion limit | |
| --- | --- | --- |
| S-200 HR | 30 bp | (5-250 kDa) |
| S-300 HR | 118 bp | (10-1500 kDa) |
| S-400 HR | 271 bp | (20-8000 kDa) |
| S-500 HR | 1078 bp | (ND) |
| S-1000 SF | 20 000 bp | (ND) |

Figure 5:
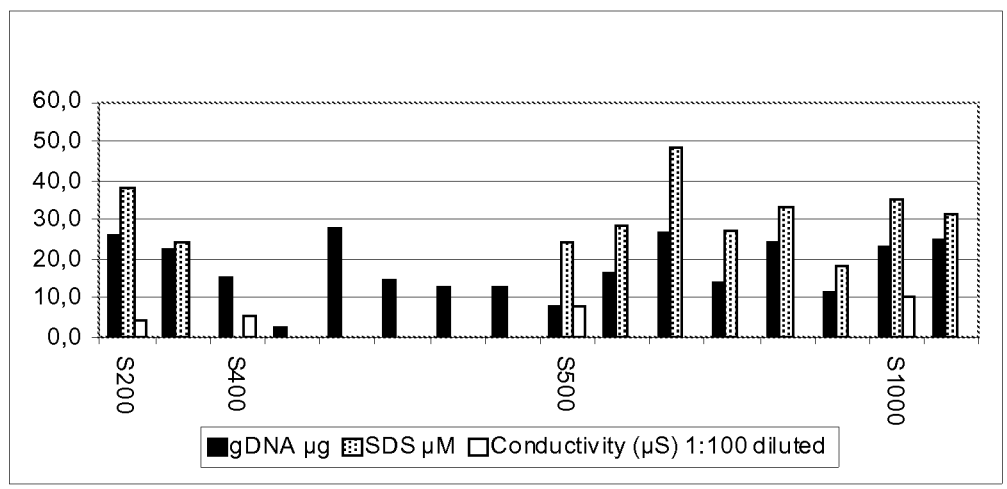
FIG. 5 shows the extent of contaminant removal by commercially available Sephacryl resins of different size exclusion limits (S200, S400, S500 and S1000) according to Example 4.

All resins were equilibrated in water prior to use: 10 mL of the resin were mixed with 40 mL of water, the resin was allowed to settle, until a sediment of 10 mL was obtained, and the supernatant (water) was discarded. This procedure was repeated three times. Finally, the volume of the suspended resin was adjusted to 10 mL by the addition of water. The columns were prepared for use by establishing the gel bed in a pre-centrifugation step (pre-spinning) at 700×g for 3 min. To each column the whole lysate, obtained from 10 mg tissue as described above, including the precipitate, was applied to the center of the gel bed's upper surface. The DNA was then eluted by spinning the column at 700×g for 3 min. Each experiment was carried out at least in duplicate. The amount of gDNA and SDS present in the eluates were measured as described above. The conductivity of the samples was determined using a diluted solution of a pooled sample, wherein all samples purified using the same resin were combined. The results are depicted in FIG. 5. All resins are suitable to significantly reduce the amount of SDS and further ions present in the sample in comparison to the filtration methods discussed above. According to Goldenberger et al. (D. Goldenberger et al. *Genome Res.* 1995, 4, 368-370) SDS concentrations in a sample exceeding 345 μmol/L completely inhibit PCR reactions. For real-time-PCR reactions the tolerable maximum amount of SDS is around 250 μmol/L. Using the S400 HR resin, it was possible to completely remove SDS from the sample. This resin also proved useful in removing residual small fragments of RNA.

Example 5

PAGE Analysis of the Eluates

Figure 6:
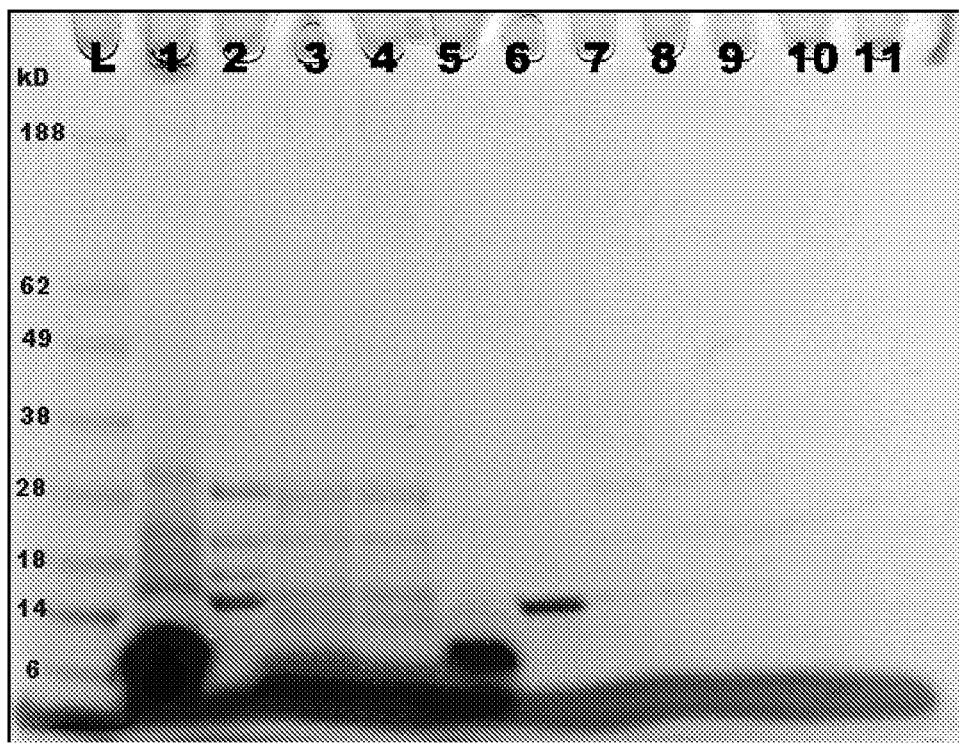
FIG. 6 shows the results as obtained according to Example 5 of a PAGE analysis of crude pork liver tissue lysate (lane 1), "precipitated" crude pork liver tissue lysate (lane 2), a lysate obtained from pork liver tissue by using the QIAamp lysis kit and RNase (lane 3), a lysate obtained from pork liver tissue by using the QIAamp lysis kit without adding RNase (lane 4), QIAGEN protease (lane 5), RNase A (lane 6), as well as eluates purified according to the present invention (lanes 7 to 9) in comparison to eluates obtained using the QIAamp kit (lanes 10 and 11). In lane L a protein standard is analyzed.

To evaluate the extent of protein removal in the purification process and to determine the residual amount of protein present in the eluate obtained after gel filtration chromatography, samples purified according to example 4 using a S400 HR resin were analyzed by PAGE analysis on a commercially available TRIS/HEPES 4-20% gradient polyacrylamide gel (LTF-LABORTECHNIK), containing SDS. The gel was run at 100 volt for 25 min in the supplied TRIS/HEPES buffer using the NOVEX XCell II system (Invitrogen GmbH, Karlsruhe, Germany). 15 μL of the samples spiked with a protein size marker were diluted with 15 μL of the 2× buffer, provided with the gel. The mixture was heated to 95° C. for 5 min, then cooled in an ice bath, and afterwards loaded into the gel pocket. The gel was stained overnight by immersing it into Gradipure stain (Gradipore, Sydney, Australia), and then rinsed with water. The results are presented in FIG. 6. The lane named "L" is a SeaBlue protein standard from Invitrogen (Karlsruhe, Germany). In lane 1, 15 μL of the crude lysate obtained from 10 mg pork liver tissue using the lysis buffer of the present invention were analyzed. In lane 2, 15 μL of the same lysate were analyzed after addition of the precipitating solution according to the present invention (without filtration step). For comparison, in lane 3 15 μL of a lysate obtained using the QIAamp Kit, additionally treated with 15 μL Rnase A, were analyzed. In lane 4, 15 μL of a lysate obtained using the QIAamp kit without adding RNase were analyzed. For comparison, the QIAGEN Protease and RNase A were analyzed in lanes 5 and 6, respectively. In each of lanes 7 to 9, aliquots of 20 μL of the eluates, obtained after purification by gel filtration chromatography according to the present invention, were analyzed (in total, 100 μL eluate were obtained). In lanes 10 and 11, an aliquot of 20 μL of the eluates obtained by using the QIAamp kit were analyzed. (in total, 400 μL eluate were obtained). It can be seen that a large amount of proteins is already co-precipitated together with SDS by the addition of strontium chloride. The remaining amount of protein can be removed efficiently by gel filtration chromatography according to the present invention, and the results obtained using the methods of the present invention are comparable to the results obtained using the commercially available QIAamp kit, especially when keeping in mind, that the dilution of the eluate obtained from the QIAamp kit is four times higher. The results obtained from lung samples and mouse tails were comparable (data not shown).

Example 6

AEX-HPLC Analysis of the Eluate

To detect minute amounts of residual contaminants such as proteins and RNA fragments, an anion exchange (AEX) HPLC analysis was performed on an TMAE-Fractogel S HPLC column using a $CaCl_2$ gradient at pH 7.2 at a flow rate of 1.5 mL/min. A gradient ranging from 0 mmol/L $CaCl_2$ to 300 mmol/L $CaCl_2$ in water, comprising 5% TRIS (pH 7.2), over 35 column volumes was established. As an injection volume 200 μL were used.

Figure 7:
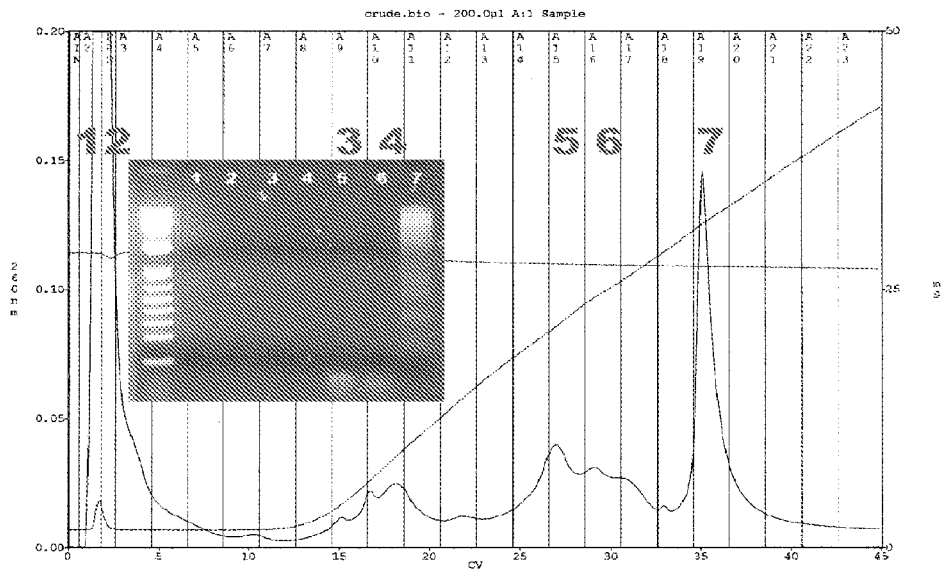
FIG. 7 shows the AEX-HPLC analysis of 200 µL of crude pork liver lysate obtained without adding RNase according to Example 6. Furthermore, an agarose gel analysis of the different fractions collected from the HPLC run is shown.

In a first experiment 200 μL of the crude lysate obtained from incubating 10 mg pork liver tissue with the buffer of the present invention in the absence of RNase were analyzed. Seven fractions were collected from the HPLC, reacted with the dye Stains-All according to the general method, and subsequently analyzed on agarose gel. The HPLC chromatogram and the photograph of the agarose gel are depicted in FIG. 7.

Fraction 1 and 2 did not react with the dye, indicating concentrations of SDS and nucleic acids below the detection limit of 21 μmol/L SDS. Fraction 3 and 4 exhibited a blue color upon addition of the dye, indicating the presence of nucleotides or soluble proteins, which cannot be stained with SYBR-Green II on an agarose gel. Fraction 5 and 6 were eluted at conductivities typical for RNA, and gave a faint band of nucleic acid smaller than 100 bp in the agarose gel, while fraction 7 contained the genomic DNA.

Figure 8:
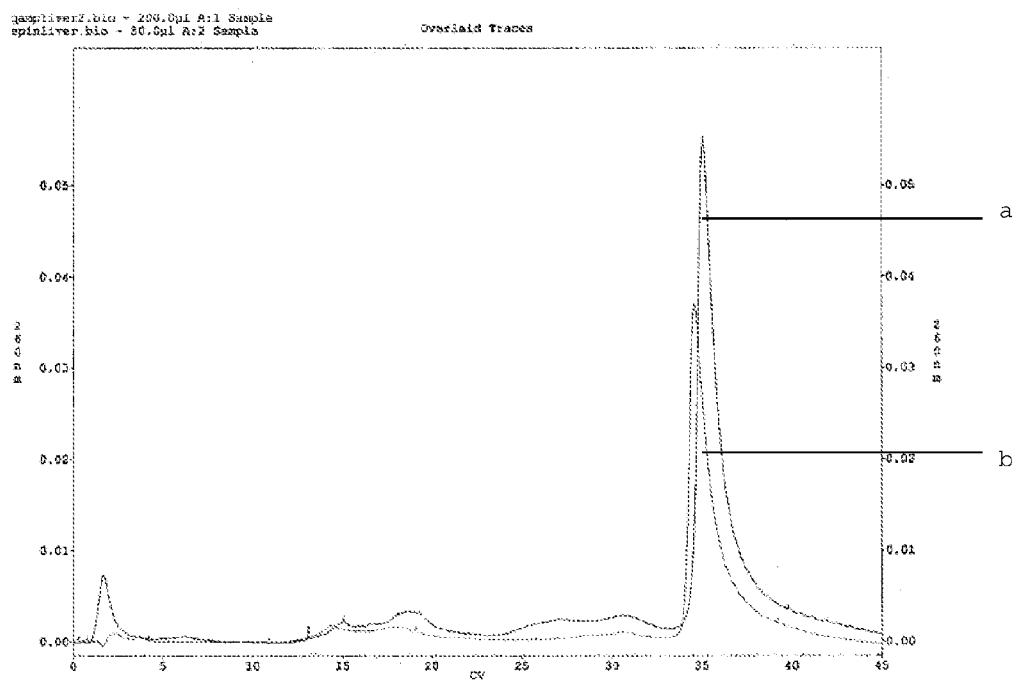
FIG. 8 shows a comparison of the HPLC profiles obtained from the eluates of samples of 10 mg fresh pork liver, purified using either a) the method of the present invention, and b) the QIAamp kit (QIAGEN, Hilden, Germany) (see Example 6). While the amount of residual contaminants is comparable in both samples, the yield of gDNA obtained by the method of the present invention is almost 50% higher (9.2 µg versus 6.2 µg), as determined using a calibration curve.

In further experiments, samples purified by the method of the present invention were compared to samples purified using the commercially available QIAamp kit by HPLC analysis. To determine the amount of genomic DNA, a calibration curve using increasing amounts of genomic E. coli DNA, purified by anion exchange chromatography, was used, correlating the area under curve (AUC) of the gDNA elution peak with the amount of gDNA loaded onto the column. In FIG. 8 the overlaid chromatograms of a sample purified using the present invention (a) and a sample purified using the QIAamp Kit (b) are presented, both traces were monitored at a wavelength of 260 nm. The yield obtained from 50 µL of the eluate purified according to the present invention (trace a in FIG. 8) is significantly higher compared to the amount of gDNA obtained from 200 µL eluate obtained by using the QIAamp Kit. (For comparison, traces a and b in FIG. 8 are normalized to a common injection volume.) This demonstrates that a high concentration of gDNA in the eluate can be achieved using the purification method according to the present invention. The amount of residual proteins and other impurities were comparable in both samples, as determined by integration of the respective peaks in the HPLC chromatogram. The amount of gDNA, present in the sample purified according to the present invention, was 9.2 µg, determined using the calibration curve, while the amount of gDNA obtained by using the QIAamp Kit was 6.2 µg.

Example 7

Figure 9:
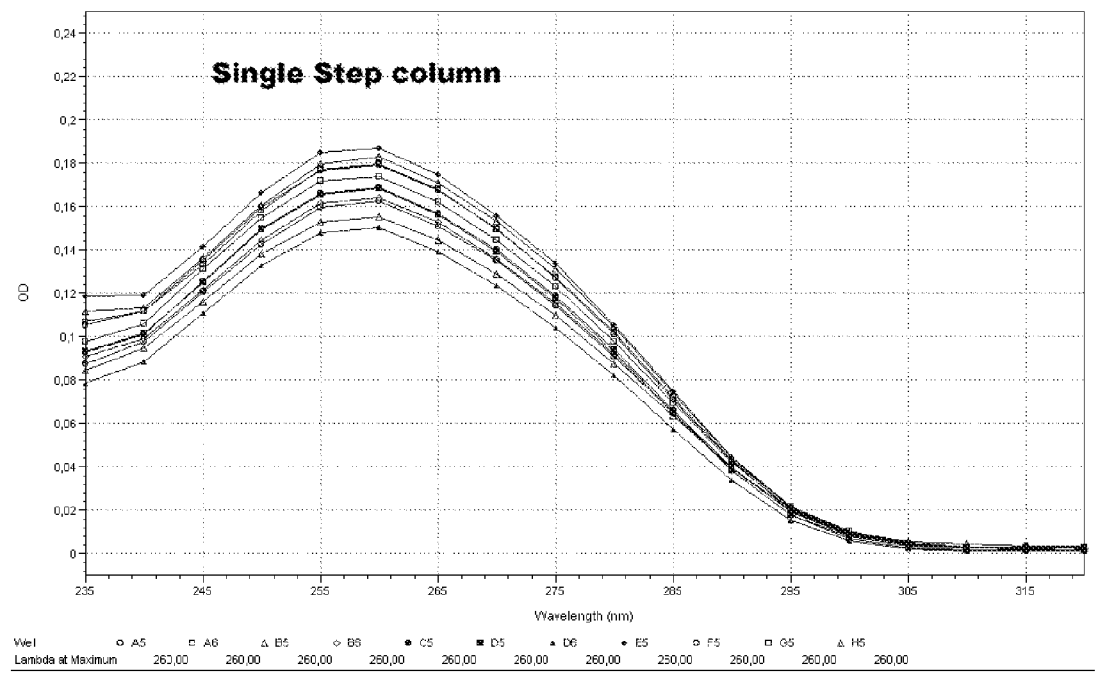
FIG. 9 shows the UV/Vis spectra of gDNA eluates, obtained by lysing and purifying 10 mg pork liver tissue, using the method of the present invention (upper spectrum), and using the QIAamp kit (lower spectrum), respectively (see Example 7).
Figure 9:
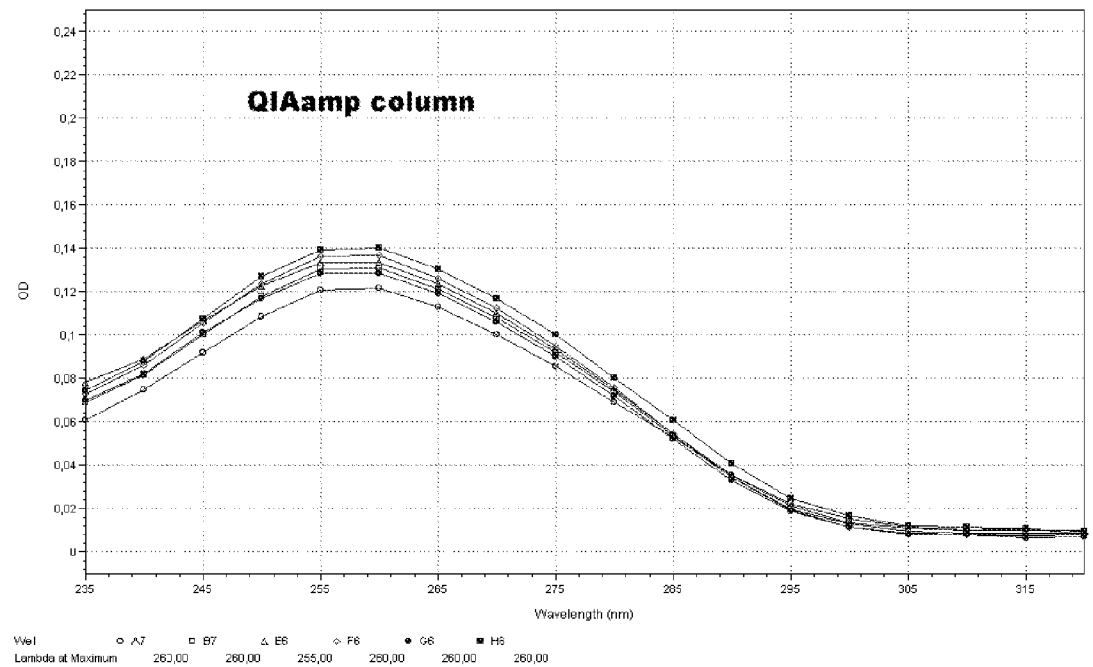

Determination of Yield and Purity of the gDNA in the Eluates Using UV/Vis Spectroscopy 12 samples of 10 mg pork liver were lysed and purified according to the method of the present invention using water as eluent in the gel filtration step, and compared to 6 samples of 10 mg pork liver purified using the QIAamp columns with the same eluent. The results are shown in FIG. 9, supporting the results obtained by HPLC analysis. The absorbance at a wavelength of 260 nm, where gDNA has its absorbance maximum, was always higher in the samples purified by the method according to the present invention than in the QIAamp purified samples. In addition, the baseline is elevated in the spectra of the QIAamp purified samples in comparison to the baseline in the spectra of the samples purified according to the present invention, which may indicate a higher amount of residual solid particles in the QIAamp samples.

Example 8

RT-PCR Analysis of Purified Rat Tail gDNA

Figure 10:
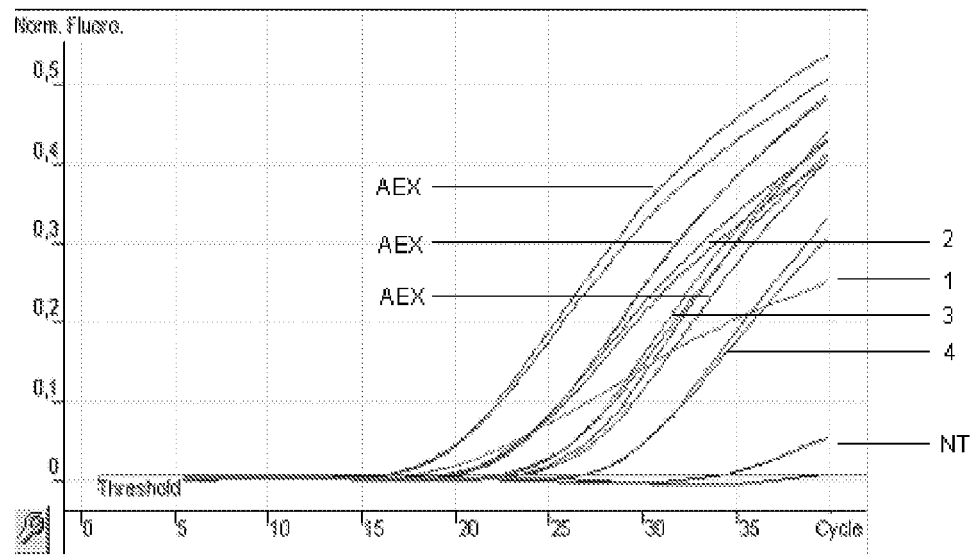
FIG. 10 shows an inhibition study (jun assay) (see Example 8) of samples isolated and purified from rat tail, using the method of the present invention. Due to the high concentration of gDNA present in the sample, a strong product inhibition is observed in the undiluted sample, and even a weak inhibition is observed in the sample which was diluted tenfold, while no inhibition was observed for samples with higher dilution.

To ensure that no PCR inhibitors are present in the samples lysed and purified according to the present invention, samples of 20 mg rat tail were lysed and purified according to the method of the present invention as detailed above. These purified samples were then analyzed in a real time PCR (RT-PCR) using the jun-system on the Rotorgene system (Corbett, Sydney, Australia) and compared to the results obtained using gDNA using AEX chromatography. A commercially available primer/probe system (FAM-TAMRA, Applied Biosystems, Darmstadt, Germany), including a 20×jun PCR primer/probe mix was used in combination with an 2×TAQman PCR universal master mix from Applied Biosystems. The RT-PCR was carried out according to the manufacturer's instruction. In particular, polymerase activation was carried out by heating the mixture for 20 min to 95° C., cycling was performed by melting the duplexes at 95° C. for 15 seconds, and annealing was carried out at 60° C. for 60 seconds. In total, 40 cycles were performed. The reaction mixture consisted of 22.5 µL of the gDNA-containing sample, 25 µL of the master mix and 2.5 µL of the primer mix. Samples obtained from the lysis and purification process of the present invention were used in an undiluted form and after dilution with water (factor 10, 100 and 1000) as a template in the PCR. Even though the undiluted sample (curve 1 in FIG. 10) showed a rather strong product inhibition due to the high concentration of gDNA in the sample, it was possible to amplify the sequence of all the samples lysed and purified by the method of the present invention, regardless of the dilution factor. The sample which had been tenfold diluted with water (curve 2) exhibited only a weak inhibition. No inhibition was observed in the samples which had been diluted 100-fold or 1000-fold prior to amplification (curves 3 and 4), respectively. For comparison, the reaction was also performed in the absence of target (no target reaction, NTC), and three samples purified by AEX chromatography were amplified under the same conditions, too.

Figure 11:
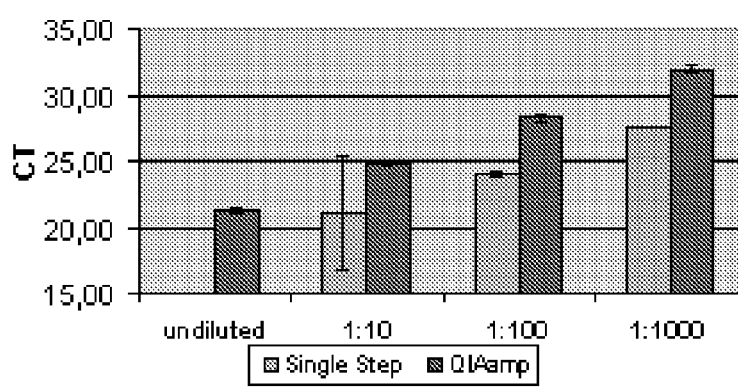
FIG. 11 shows the CT-values obtained according to Example 8 from a qRT-PCR reaction amplifying the lysate obtained from 10 mg rat liver tissue using the method of the present invention (denoted as "single step"), and using the QIAamp kit in a jun assay on a TAQman 7700 analyzer. Again a product inhibition was observed in the undiluted and in the tenfold diluted samples purified with the method of the present invention. However, with diluted samples the CT-values were always lower for the lysates obtained according to the method of the present invention.

Similar results were obtained with samples derived from 10 mg frozen liver tissue, lysed and purified according to the present invention in comparison to samples lysed and purified using the QIAamp kit. FIG. 11 shows a comparison of the CT-values obtained in RT-PCT of these samples in a jun essay using different dilutions of the purified samples. Again, a product inhibition is observed in the reaction using the undiluted samples purified by the present invention. The CT-values obtained from 10-fold, 100-fold and 1000-fold diluted samples, respectively, purified according to the present invention are always lower than the CT-values obtained using the QIAamp purified samples, indicating a higher amount of gDNA present in the samples purified according to the present invention.

A jun assay was also performed using samples that were lysed according to the present invention with subsequent SDS removal by precipitation, but that were not further purified using the gel filtration step. In this assay undiluted, 2-4- and 8-fold dilutions were completely inhibited. However, amplification from a 16-fold diluted solution was possible.

Example 9

Comparison of the Yield of gDNA Obtained from Different Tissue Samples by the Method of the Present Invention and by Using the QIAamp Kit Samples of the different tissues listed in Table 2 were lysed according to the present invention and SDS was subsequently precipitated from the lysate by adding strontium ions, or the samples were lysed according the QIAamp protocol. After lysis (and precipitation in the case of the present invention), the samples obtained from the same kind of tissue by the same purification method were pooled, and then split into 100 µL aliquots. These aliquots were purified according to the method of the present invention or according to the QIAamp protocol, respectively. The amount of gDNA present in the sample was analyzed by UV/Vis spectroscopy and/or HPLC analysis. The average results obtained are given in Table 2.

TABLE 2

| Sample | yield [µg] present invention | yield [µg] QIAamp | detection method |
|---|---|---|---|
| 10 mg pork liver | 18.3 | 12.4 | HPLC |
| 10 mg mouse lung | 6.9 | 4.3 | UV/Vis |
| 20 mg mouse tail | 18.5 | 6.5 | UV/Vis |
| 10 mg mouse kidney | 25.5 | 8.7 | UV/Vis |
| 5 mg mouse spleen | 36.6 | not determined | UV/Vis |

TABLE 2-continued

| Sample | yield [μg] present invention | yield [μg] QIAamp | detection method |
|---|---|---|---|
| 10 mg mouse spleen | 66.0 | not determined | UV/Vis |
| 10 mg rat tail | 8.7 | 6.5 | UV/Vis |
| 20 mg rat tail | 11.7 | not determined | HPLC |
| 10 mg pork muscle | 5.8 | 1.5 (0.5) | UV/Vis (HPLC) |
| 50 mg bovine pancreas | 4.5 | 0 | UV/Vis |
| 10 mg rat liver | 30.2 (4.6) | 4.6 (2.0) | UV/Vis (HPLC) |

Example 10

Lysis and Purification of Human Blood Samples

Figure 12:
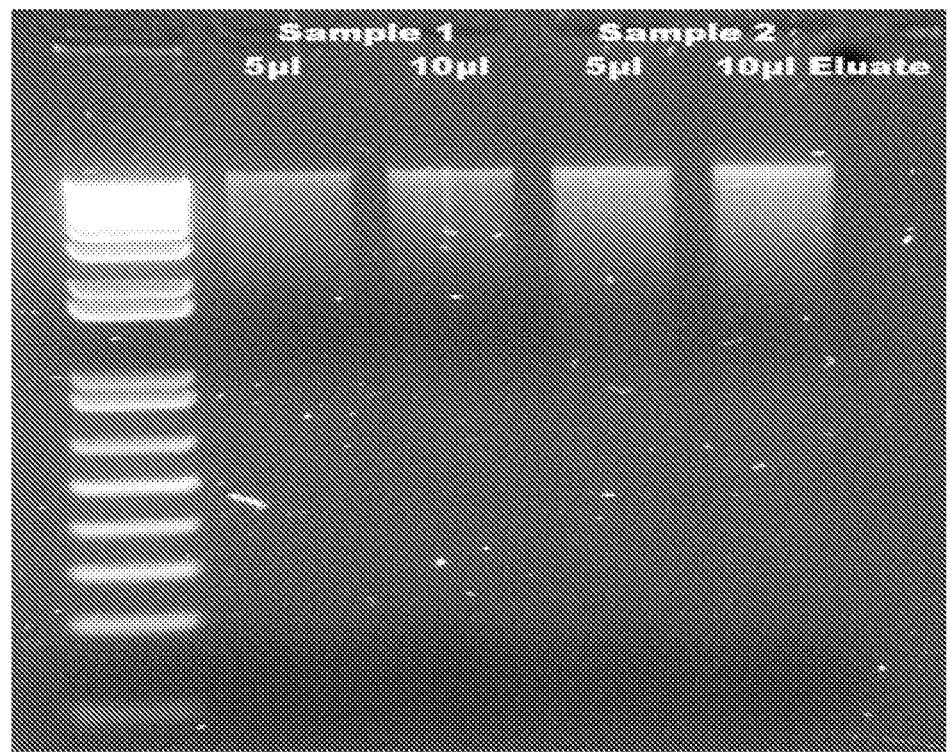
FIG. 12 shows a SYBR-green II stained agarose gel of two blood samples purified by the method of the present invention (see Example 10). As a reference, a DNA length standard (GIBCO 1 kb plus DNA ladder, Invitrogen GmbH, Karlsruhe, Germany) is shown on the left hand side.

Due to the high liquid content of blood samples, a twofold concentrated lysis buffer (2×) comprising 50 mmol/L TRIS and 50 mmol/L SDS, adjusted to pH 8.5 by the addition of $H_2SO_4$, was used for lysis of the cells. Two samples of 40 μL of human blood from the same donor were mixed with an equal amount of the 2× lysis buffer. Blood proteins were then depleted by addition of 10 μL QIAGEN Protease (2.5 AU/ml). The samples were incubated at 62° C. for 10 min. SDS was removed from the lysates by precipitation as described above, and the samples were purified by gel filtration chromatography using the spin columns of the present invention. Aliquots of 5 μL and 10 μL were then analyzed on an agarose gel (FIG. 12). The gDNA band is visible in all samples analyzed, and no shorter fragments can be detected.

Quantification of the amount of gDNA present within the samples revealed an average yield of 600 ng gDNA in the samples using 18 S gDNA primers (for each of the two samples RT-PCR was carried out in duplicate, and the amount of gDNA was determined as an average value from all four experiments).

Example 11

Figure 13:
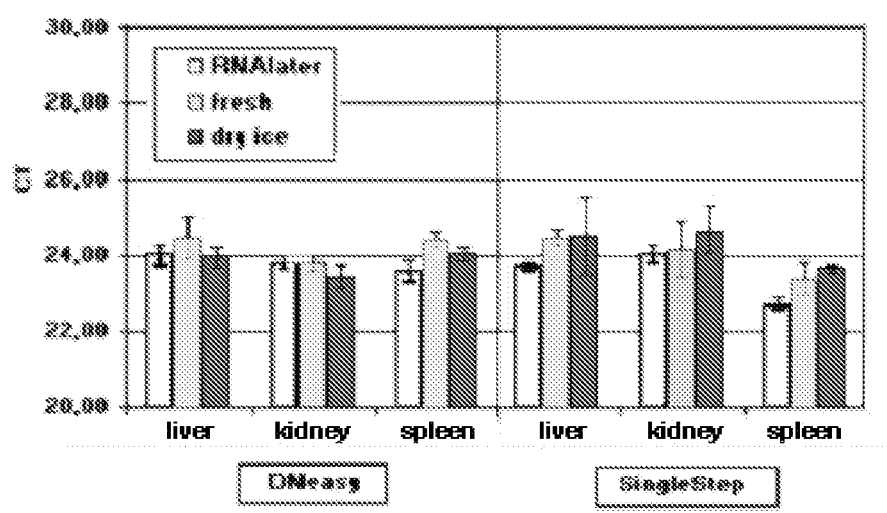
FIG. 13 shows a comparison of the RT-PCR results obtained from liver, kidney and spleen tissue samples, either stored in the commercially available RNA later reagent (QIAGEN, Hilden, Germany), being frozen on dry ice (−78° C.) prior to use, or used as received (fresh sample). The samples were lysed and purified using the commercially available DNeasy kit (QIAGEN, Hilden, Germany) (left hand side), and the method of the present invention (right hand side, denoted as "single step") as described in Example 11. It can be seen that the CT-values obtained in the RT-PCR reaction are comparable for both methods.

RT-PCR of Different Animal Tissue Samples 50 ng (as estimated by UV/Vis spectroscopy) of purified gDNA obtained from rat liver, kidney and spleen tissue that was lysed and purified using the method of the present invention, or according to the DNeasy protocol using a commercially available DNeasy kit (QIAGEN, Hilden, Germany) were used as targets for RT-PCR. Fresh and frozen tissue samples, and samples stabilized in the commercially available RNAlater reagent (QIAGEN, Hilden, Germany) were used. The samples were then analyzed in a SYBR-Green-based RT-PCR reaction on a TAQman system. As can be seen in FIG. 13, the CT-values obtained in the RT-PCR reaction are comparable for both methods, regardless of the kind of sample analyzed (fresh, frozen and stabilized in RNAlater, respectively). An elution buffer, comprising 10 mmol/L TRIS/HCl and 0.5 mmol/L EDTA, adjusted to pH 9.0, was used to equilibrate the spin columns according to the procedure described above and as an eluent.

Example 12

Figure 14:
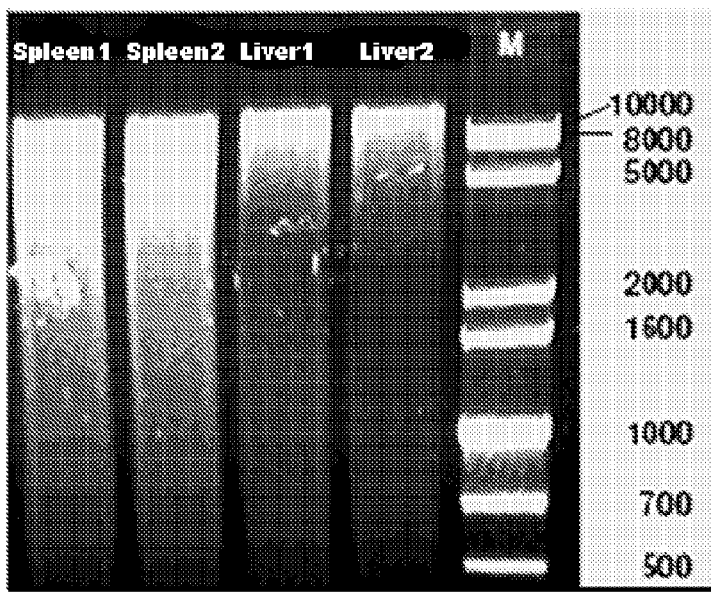
FIG. 14 shows an agarose gel of the eluates obtained from lysis and purification of liver and spleen tissue according to the present invention (see Example 12).

Purification of High Molecular Weight gDNA from Liver and Spleen Samples 20 mg of rat liver and spleen tissue, respectively, were lysed and purified according to the present invention. Lysis was complete within 30 min. Each experiment was carried out in duplicate. Quality of gDNA in the lysates obtained were analyzed in a PCR reaction and on an ethidium bromide stained agarose gel (FIG. 14), which clearly shows a gDNA band of high molecular weight, even though the gel was overloaded. The amount of gDNA present in the samples as well as the purity, estimated by the ratio of the absorbance of the sample at a wavelength of 260 nm to the absorbance at a wavelength of 280 nm are presented in Table 3. High amounts of gDNA of good purity were obtained, even though reaction conditions were not finally optimized.

TABLE 3

| Sample | ng DNA/μL eluate | A260 | A260/A280 |
|---|---|---|---|
| liver 1 | 654.29 | 3.089 | 1.84 |
| liver 2 | 621.75 | 12.44 | 1.72 |
| spleen 1 | 1330.87 | 26.62 | 1.85 |
| spleen 2 | 1494.49 | 29.89 | 1.82 |

Example 13

Comparison of Different Column Buffers

Figure 15:
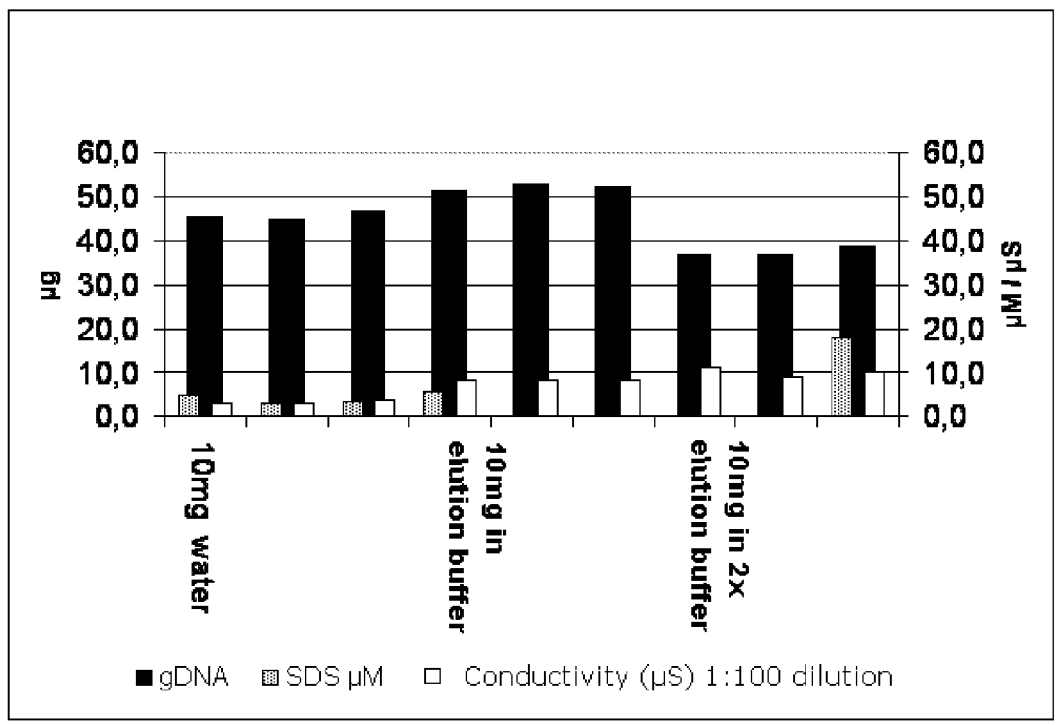
FIG. 15 shows the amount of gDNA (in µg) and SDS (in µM) and the conductivity (in µS after dilution) in the eluates obtained from lysis and purification of rat liver tissue according to the present invention using water, buffer AE and a twofold concentrated buffer AE as an eluant in the gel filtration step as shown in Example 13.

Samples of 10 mg of frozen rat liver tissue each were lysed according to the present invention. After addition of the precipitating agent the samples were purified by gel filtration chromatography, using the columns described in co-pending application with the title "chromatographic device and method for isolating and purifying nucleic acids" of the same applicant having the same filing date as the present application, equilibrated in water and buffer AE, respectively. In addition, several samples were lysed in a twofold concentrated lysis buffer according to the present invention and purified by gel filtration chromatography using the aforementioned spin columns equilibrated in the elution buffer of example 11. The eluates obtained were analyzed by gel electrophoresis and the amount of gDNA, and SDS as well as the conductivity of the eluates were determined. SDS was only detected in five samples. The results are presented in FIG. 15.

Example 14

Isolation and Purification of gDNA from FFPE-Tissue Samples

Samples of 10 μm thickness from a formalin fixed paraffin embedded (FFPE) block of rat liver were lysed, and the gDNA was isolated and purified using a) a commercially available QIAamp kit (QIAGEN, Hilden, Germany) and b) using the method of the present invention.

a) Three sections with each 10 μm from the FFPE block were lysed in 1 mL xylene, mixed by vortexing for 10 s, and centrifuged at full speed for 2 min. The supernatant was removed by pipetting. Residual xylene was extracted by adding 1 mL EtOH to each sample, vortexing the samples for 10 s, centrifuging them at full speed for 2 min and removing the supernatant. The open tubes containing the samples were incubated at room temperature for 20 min to evaporate residual EtOH. The pellets obtained were resuspended in 180 μL buffer ATL (QIAGEN, Hilden, Germany). To each sample 20 μL of Proteinase K (2.5 AU/ml) (QIAGEN, Hilden, Germany) were added, and the samples were mixed by vortexing. The samples were incubated at 56° C. for 1 h before incubating them at 90° C. for 1 h. The samples were cooled to room temperature, then 1 μL of RNase A (10 U/ml) (QIAGEN, Hilden, Germany) was added to each sample. 200 μL buffer AL (QIAGEN, Hilden, Germany) was added to each lysate, and the samples were mixed thoroughly by vortexing. 200 µL EtOH were then added, and the samples were vortexed again. The lysates were transferred to a QIAamp MinElute column (QIAGEN, Hilden, Germany) and centrifuged at 6000×g for 1 min. The QIAamp MinElute column was placed into a clean 2 mL collection tube and the flow-through was discarded. The column was opened and washed with 500 µL buffer AW1 (QIAGEN, Hilden, Germany) and centrifuged at 6000×g for 1 min. The QIAamp MinElute column was placed into a clean 2 mL collection tube and the flow-through was discarded. The column was opened again and washed with 500 µl buffer AW2 (QIAGEN, Hilden, Germany) and centrifuged at 6000×g for 1 min. The QIAamp MinElute column was placed into a clean 2 mL collection tube and the flow-through was discarded. The membrane was centrifuged at full speed for 3 min to remove traces of buffer. Elution of the gDNA was done in a clean 1.5 ml micro centrifuge tube with 100 µl RNase-free water by incubation at room temperature for 1 min and centrifugation at full speed for 1 min.

b) Three sections with each 10 µm thickness from the FFPE block were lysed in 80 µL of the lysis buffer according to the present invention (25 mmol/l Tris/$H_2SO_4$, 25 mmol/L SDS, pH 8.5), supplemented with 10 µL QIAGEN Protease (2.5 AU/ml) (Hilden, Germany) and 1 µL RNase A (7000 U/ml). The samples were mixed by vortexing. Three samples were incubated at 62° C. for 30 min and then at 90° C. for 1 h, while the other three samples were incubated at 56° C. for 1 h before incubating them at 90° C. for 1 h. To each sample 10 µL of the precipitating solution (1 mol/L $SrCl_2$) was added, and the samples were mixed by vortexing and incubated on ice for 10 min. Each sample was then transferred to a pre-spun spin column according to copending application with the title "chromatographic device and method for isolating and purifying nucleic acids" of the same applicant having the same filing date as the present application ("single-step column"), and the column was centrifuged at 700×g for 3 min, while the eluate containing the gDNA was collected.

Figure 16:
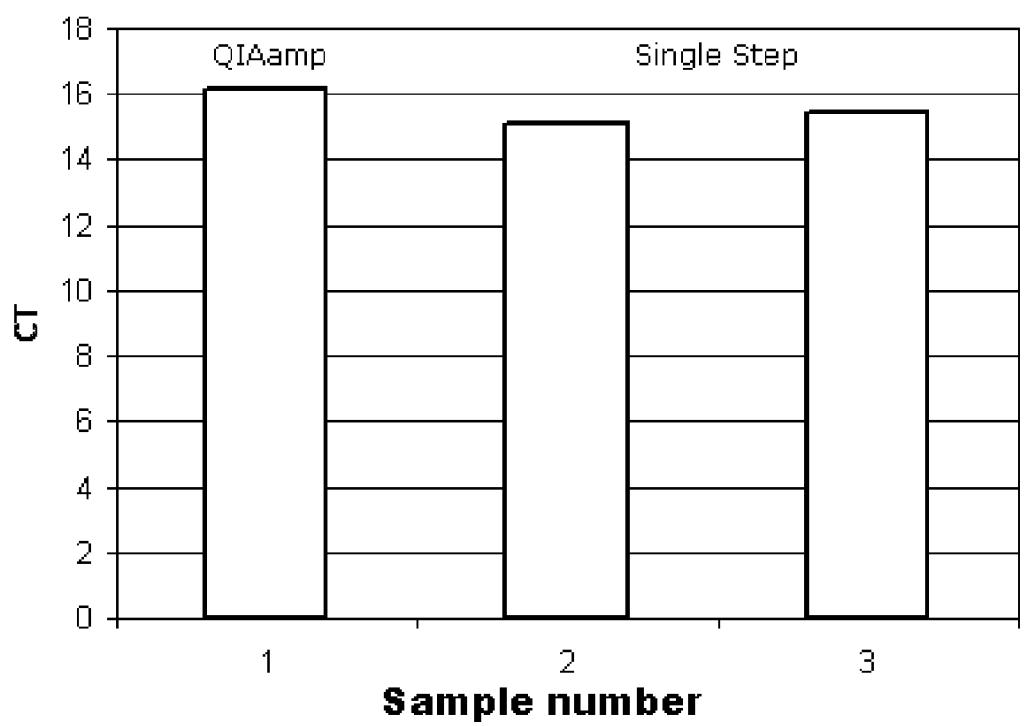
FIG. 16 shows the CT-values of an RT-PCR of a gene coding for 18S rRNA from FFPE rat liver tissue (Example 14). Sections from the FFPE block were lysed and purified using a commercially available kit (1) and the method of the present invention (2 and 3).
Figure 17:
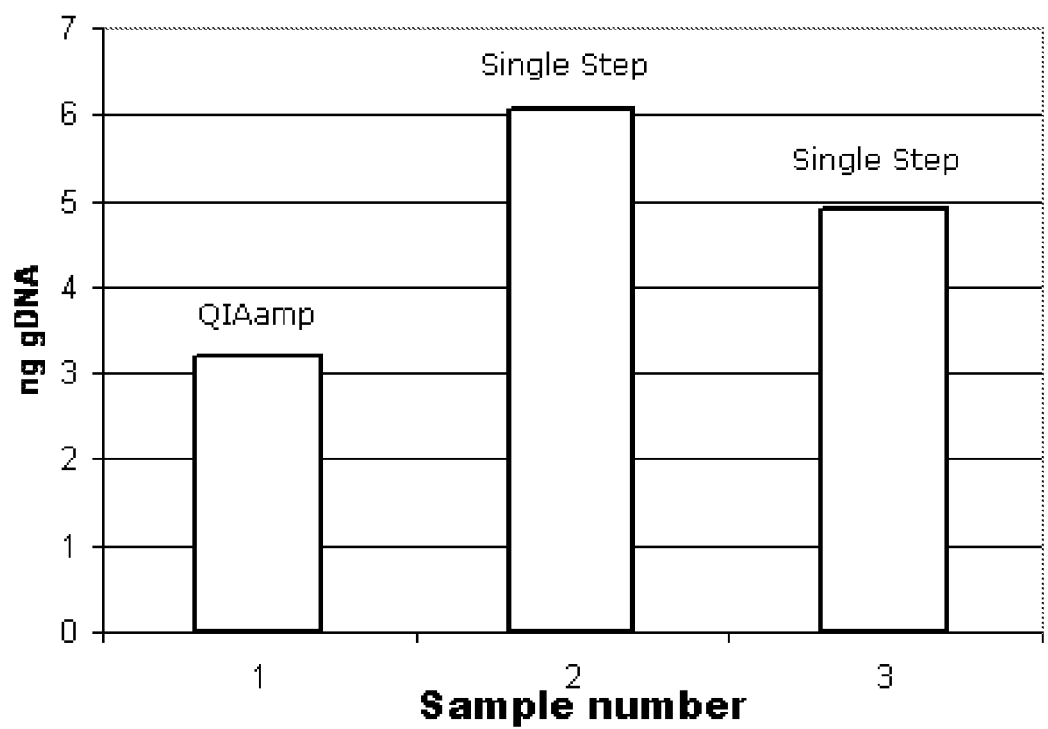
FIG. 17 shows the amount of gDNA obtained from FFPE rat liver tissue (Example 14) using a commercially available kit (1) and the method of the present invention (2 and 3).

To evaluate the amount and quality of the gDNA obtained, a SYBR Green-based RT-PCR was carried out on a TAQman system using the gene coding for 18 S rRNA as a target. The results are presented in FIGS. 16 and 17. While the CT-values obtained in the RT-PCR are comparable for both methods (the samples purified by the present invention having a slightly lower CT-value), the amount of gDNA obtained by using the method of the present invention is about 1.5-fold to about almost twice as a high as the amount of gDNA obtained by using the kit commercially available. As can be seen from FIG. 17, extending the lysis time to 1 h has an advantageous effect on the yield of gDNA obtained from FFPE samples.

The invention claimed is:

1. A method of lysing cells in a cell-containing biological sample comprising the steps of:
   (1) mixing the sample with a lysis buffer, wherein the lysis buffer comprises a buffering substance, $H_2SO_4$ and a source of anionic surfactant ions, the buffer has a pH of 7.5 to 10, 8 to 9, or 8.5, and is essentially free of EDTA and $Mg^{2+}$ ions,
   (2) incubating the mixture obtained in step (1) to obtain a lysate that comprises at least DNA, RNA and proteins, and is essentially free of a chelating or complexing agent, and
   (3) precipitating the surfactant ions out of the lysate.

2. The method according to claim 1, additionally comprising a step of disintegrating the RNA contained in the lysate.

3. The method according to claim 2, wherein the step of incubating the mixture to obtain a lysate and the step of disintegrating the RNA from the sample are carried out in a single step by heating the mixture to a temperature above 60° C.

4. The method according to claim 3, wherein the mixture is heated for 10 to 80 min, 15 to 60 min, 20 to 50 min, or 30 to 45 min.

5. The method according to claim 1, wherein a lysis buffer volume of 20 to 150 µL, 30 to 120 µL, to 100 µL, or 80 µL is used for the lysis of 10 mg sample tissue.

6. The method according to claim 1, wherein the sample is a cell-containing biological sample.

7. The method according to claim 6, wherein the tissue is mammalian tissue.

8. A method for isolating and purifying nucleic acids, from a biological sample comprising nucleic acids and contaminants, comprising the steps of:
   (1) mixing the sample with a lysis buffer, wherein the lysis buffer comprises a source of anionic surfactant ions, but is essentially free of a chelating or complexing agent,
   (2) incubating the mixture obtained in step (1) to obtain a lysate that comprises DNA, RNA and proteins, and is essentially free of a chelating or complexing agent,
   (3) optionally disintegrating the RNA present in the lysate,
   (4) precipitating the surfactant ions out of the lysate, and
   (5) separating the nucleic acids from the precipitate and further contaminants present in the lysate to obtain a purified nucleic acid-containing eluate.

9. The method according to claim 8, wherein the step of incubating the mixture to obtain a lysate and the step of disintegrating the RNA from the sample are carried out in a single step by heating the mixture to a temperature above 60° C.

10. The method according to claim 9, wherein the mixture is heated for 10 to 80 min, 15 to 60 min, 20 to 50 min, or 30 to 45 min.

11. The method of claim 9, wherein the temperature above 60° C. is 60° C. to 70° C., 61° C. to 65° C., or 62° C.

12. The method according to claim 8, wherein a lysis buffer volume of 20 to 150 µL, 30 to 120 µL, 50 to 100 µL, or 80 µL is used for the lysis of 10 mg sample tissue.

13. The method according to claim 8, wherein the sample is a cell-containing biological sample.

14. The method of claim 13, wherein the cell-containing biological sample is selected from the group consisting of fresh or frozen tissue, blood, and Gram-negative bacteria.

15. The method according to claim 13, wherein the tissue is mammalian tissue.

16. The method of claim 15, wherein the mammalian tissue is human tissue.

17. The method of claim 8, wherein step (4) is performed by adding to the lysate a solution comprising monovalent ions of alkali metals and/or divalent ions of alkaline earth metals selected from the group consisting of $Rb^+$, $Cs^+$, $Ca^{2+}$, $Sr^{2+}$, $Ba^{2+}$, or a mixture thereof.

18. The method of claim 8, wherein step (5) is performed by size exclusion chromatography to obtain a purified nucleic acid-containing eluate.

19. The method of claim 8, wherein the lysis buffer comprises a buffering substance, $H_2SO_4$ and a source of anionic surfactant ions, the buffer has a pH of 7.5 to 10, 8 to 9, or 8.5, and is essentially free of EDTA and $Mg^{2+}$ ions.

20. The method of claim 8, wherein the nucleic acids of step (5) comprise DNA.

21. The method of claim 8, wherein the nucleic acids of step (5) comprise genomic DNA.

* * * * *